United States Patent
Barnhart et al.

(10) Patent No.: US 11,103,579 B2
(45) Date of Patent: Aug. 31, 2021

(54) COMBINATION OF DR5 AGONIST AND ANTI-PD-1 ANTAGONIST AND METHODS OF USE

(71) Applicant: BRISTOL-MYERS SQUIBB COMPANY, Princeton, NJ (US)

(72) Inventors: Bryan Barnhart, San Francisco, CA (US); Maria N. Jure-Kunkel, Plainsboro, NJ (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 154 days.

(21) Appl. No.: 15/993,687

(22) Filed: May 31, 2018

(65) Prior Publication Data
US 2018/0360962 A1 Dec. 20, 2018

Related U.S. Application Data

(63) Continuation of application No. 14/774,382, filed as application No. PCT/US2014/024208 on Mar. 12, 2014, now abandoned.

(60) Provisional application No. 61/783,184, filed on Mar. 14, 2013.

(51) Int. Cl.
*A61K 39/395* (2006.01)
*C07K 16/28* (2006.01)
*A61K 39/00* (2006.01)

(52) U.S. Cl.
CPC .... *A61K 39/39558* (2013.01); *C07K 16/2818* (2013.01); *C07K 16/2827* (2013.01); *C07K 16/2878* (2013.01); *A61K 2039/507* (2013.01); *A61K 2039/545* (2013.01)

(58) Field of Classification Search
CPC ........ A61K 2039/545; A61K 2039/507; A61K 39/39558; C07K 2317/76; C07K 2317/75; C07K 2317/70
USPC ...................................................... 424/133.1
See application file for complete search history.

(56) References Cited

U.S. PATENT DOCUMENTS

| | | |
|---|---|---|
| 1,763,223 A | 6/1998 | Wiley et al. |
| 6,046,048 A | 4/2000 | Ashkenazi et al. |
| 6,072,047 A | 6/2000 | Rauch et al. |
| 6,153,402 A | 11/2000 | Yu et al. |
| 6,214,580 B1 | 4/2001 | Ni et al. |
| 6,284,236 B1 | 9/2001 | Wiley et al. |
| 6,342,363 B1 | 1/2002 | Ni et al. |
| 6,417,328 B2 | 7/2002 | Alnemri |
| 6,433,147 B1 | 8/2002 | Ni et al. |
| 6,461,823 B1 | 10/2002 | Ni et al. |
| 6,469,144 B1 | 10/2002 | Ashkenazi |
| 6,506,569 B1 | 1/2003 | Ni et al. |
| 6,521,228 B1 | 2/2003 | Wiley et al. |
| 6,569,642 B1 | 5/2003 | Rauch et al. |
| 6,607,726 B1 | 8/2003 | Ni et al. |
| 6,642,358 B1 | 11/2003 | Rauch et al. |
| 6,713,061 B1 | 3/2004 | Yu et al. |
| 6,740,739 B1 | 5/2004 | Ashkenazi et al. |
| 6,743,625 B2 | 6/2004 | Ni et al. |
| 6,759,513 B2 | 7/2004 | Yu et al. |
| 6,872,568 B1 | 3/2005 | Ni et al. |
| 6,902,910 B2 | 6/2005 | Ni et al. |
| 6,943,020 B2 | 9/2005 | Ni et al. |
| 6,951,735 B2 | 10/2005 | Yu et al. |
| 6,969,599 B2 | 11/2005 | Ni et al. |
| 7,060,272 B2 | 6/2006 | Ni et al. |
| 7,064,189 B2 | 6/2006 | Salcedo et al. |
| 7,357,927 B2 | 4/2008 | Yu et al. |
| 7,528,239 B1 | 5/2009 | Rauch et al. |
| 7,943,743 B2 | 5/2011 | Korman et al. |
| 8,008,449 B2 | 8/2011 | Korman et al. |
| 9,265,765 B2 | 2/2016 | Stogniew et al. |
| 9,376,437 B2 | 6/2016 | Stogniew et al. |
| 2002/0098550 A1 | 7/2002 | Ni et al. |
| 2016/0067337 A1 | 3/2016 | Barnhart et al. |
| 2018/0326098 A1* | 11/2018 | Donnelly .............. C07B 59/002 |
| 2020/0055936 A1* | 2/2020 | Johnston ............ C07K 16/2812 |
| 2020/0079848 A1* | 3/2020 | Schebye ............ C07K 16/2827 |

FOREIGN PATENT DOCUMENTS

| | | |
|---|---|---|
| EP | 1434881 A2 | 7/2004 |
| WO | 97/01633 A1 | 1/1997 |
| WO | 97/33904 A1 | 9/1997 |
| WO | 97/37020 A1 | 10/1997 |
| WO | 98/32856 A1 | 7/1998 |
| WO | 98/35986 A1 | 8/1998 |
| WO | 98/041629 A2 | 9/1998 |
| WO | 98/46643 A1 | 10/1998 |
| WO | 98/51793 A1 | 11/1998 |
| WO | 98/54202 A1 | 12/1998 |
| WO | 98/58062 A1 | 12/1998 |
| WO | 99/09165 A1 | 2/1999 |
| WO | 99/36535 A1 | 7/1999 |

(Continued)

OTHER PUBLICATIONS

Jazirehi et al. (J Immunol. Apr. 15, 2014; 192(8): 3981-3989. doi:10.4049/jimmunol.1302532).*

(Continued)

*Primary Examiner* — Lynn A Bristol

(74) *Attorney, Agent, or Firm* — Nelson Mullins Riley & Scarborough LLP; Jane E. Remillard, Esq.; Jeanne M. DiGiorgio, Esq.

(57) ABSTRACT

Provided are methods and compositions for treating cancer using an effective amount of a PD-1 antagonist in combination with a DR4 or DR5 agonist.

14 Claims, 3 Drawing Sheets

Specification includes a Sequence Listing.

(56) References Cited

FOREIGN PATENT DOCUMENTS

| WO | 00/66156 A1 | 11/2000 |
|---|---|---|
| WO | 00/67793 A1 | 11/2000 |
| WO | 00/73321 A1 | 12/2000 |
| WO | 02/97033 A2 | 12/2002 |
| WO | 03/025138 | 3/2003 |
| WO | 03/54216 A2 | 7/2003 |
| WO | 04/16753 A2 | 2/2004 |
| WO | 05/16326 A2 | 2/2005 |
| WO | 2007/005874 A2 | 1/2007 |
| WO | 2014159562 A1 | 10/2014 |

OTHER PUBLICATIONS

Izquierdo et al. (Miscoscopy (Oxf); Abtractonly; p. 1 (2016)).*
DeCorte et al. ((nstitute of Professional Representatives before the European Patent Office/European Patent Institute/epi ; 1 (19): (2019).*
Clinicaltrials.gov (Study of DS-8273a With Nivolumab in Unresectable Stage III or Stage IV Melanoma; pp. 1-10 (Apr. 21, 2021).*
Ashkenazi, A., et al, "To Kill a Tumor Cell: The Potential of Proapoptotic Receptor Agonists," The Journal of Clinical Investigation, vol. 118, 2008, pp. 1979-1990.
Beckman, RA et al., "Antibody constructs in cancer therapy: protein engineering strategies to improve exposure in solid tumors," Cancer, vol. 109(2):170-179 (2007).
Cespdes, MV., et al., "Mouse models in oncogenesis and cancer therapy," Clin. Transl. Oncol., vol. 8(5):318-329 (2006).
Chen, H., et al., "A Novel Multimeric Protein Scaffold Stimulates Apoptotic Signaling Through TRAILR2," AACR Annual Meeting, 2012, Presentation Abstract, Abstract No. 239, 1 page.
Croft, M. et al., "Clinical Targeting of the TNF and TNFR Superfamilies," Nature Reviews, vol. 12, 2013, pp. 147-168.
Demarest, Stephen J. et al., "Emerging antibody combinations in oncology," MABS, Landes Bioscience, US, vol. 3, No. 4, Jul. 1, 2011, pp. 338-351, XP002690158.
Dennis, C. "Cancer: off by a whisker," Nature, vol. 442(7104):739-741 (2006).
Fujimori, K. et al., "A modeling analysis of monoclonal antibody percolation through tumors: a binding-site barrier," J. Nuc. Med., vol. 31(7):1191-1198 (1990).
Hellwig, C., et al., "TRAIL Signaling and Synergy Mechanisms Used in TRAIL-Based Combination Therapies," Mol. Cancer Therapy, vol. 11, 2012, pp. 3-13.
Huet, H., et al., "TAS266, a novel tetrameric nanobody agonist targeting death receptor 5 (DR5), elicits superior antitumor efficacy that conventional DR4-targeted approaches," AACR Annual Meeting, 2012, Presentation Abstract, Abstract No. 3853, pp. 1.
International Preliminary Report on Patentability, PCT/US2014/024208, dated Sep. 15, 2015, pp. 1-6.
International Search Report, PCT/US2014/024208, dated Jun. 27, 2014, pp. 1-4.
Melero, I. et al., "Palettes of Vaccines and Immunostimulatory Monoclonal Antibodies for Combination," Clinical Cancer Research, vol. 15, No. 5, 2009, pp. 1507-1509.
Rudnick, SI, et al. "Affinity and avidity in antibody-based tumor targeting," Can. Biotherp. & Radiopharm., vol. 24(2): 155-162 (2009).
Takeda, K. et al., "Combination antibody-based cancer immunotherapy," Cancer Sci., vol. 98, No. 9, 2007, 1297-1302.
Takeda, K. et al., Combination Therapy of Established Tumors by Antibodies Targeting Immune Activating and Suppressing Molecules, The Journal of Immunology, vol. 184, No. 10, Apr. 16, 2010, pp. 5493-5501, XP055123617.
Talmadge, JE, et al., "Murine models to evaluate novel and conventional therapeutic strategies for cancer," Am. J. Pathol., vol. 170(3):793-804 (2007).
Thurber, GM, et al., "Antibody tumor penetration: transport opposed by systemic and antigen-mediated clearance.," Adv. Drug Deliv. Rev., vol. 60(12):1421-1434 (2008).
Uno, T., et al., "Eradication of established tumors in mice by a combination antibody-based therapy," Nature Medicine, vol. 12, No. 6, May 7, 2006, pp. 693-698, XP055123624.
Vanneman, Matthew, et al., "Combining immunotherapy and targeted therapies in cancer treatment," Nature Reviews Cancer, vol. 12, No. 4, Jan. 1, 2012, pp. 237-251, XP055045378.
Verbrugge, I. et al., "Enhancing the Antitumor Effects of Radiotherapy with Combinations of Immunostimulatory Antibodies," OncoImmunology, vol. 9, No. 1, 2012, pp. 1629-1631.
Voskoglou-Nomikos, T. et al., "Clinical predictive value of the in vitro cell line, human xenograft, and mouse allograft preclinical cancer models," Clin. Can. Res., vol. 9(111):4227-4239 (2003).
U.S. Appl. No. 14/774,382, filed Sep. 10, 2015, Bryan Barnhart.
U.S. Appl. No. 14/774,382, Jun. 16, 2017, L. Bristol.
U.S. Appl. No. 14/774,382, Jan. 26, 2017, L. Bristol.
U.S. Appl. No. 14/774,382, Aug. 19, 2016, L. Bristol.
U.S. Appl. No. 14/774,382, Aug. 1, 2016, L. Bristol.

* cited by examiner

Figure 2A
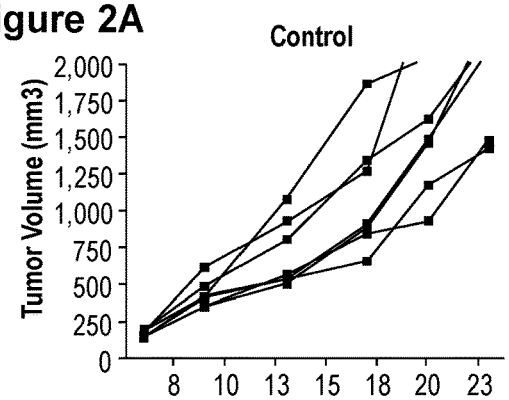
Control
Figure 2B
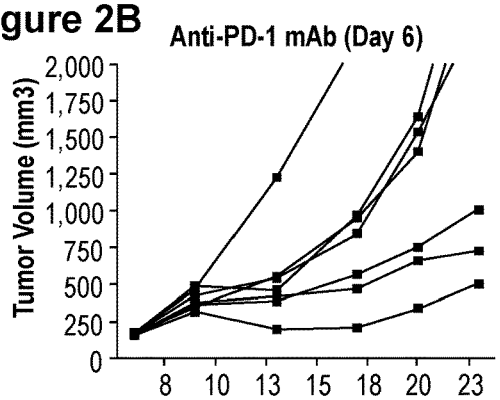
Anti-PD-1 mAb (Day 6)
Figure 2C
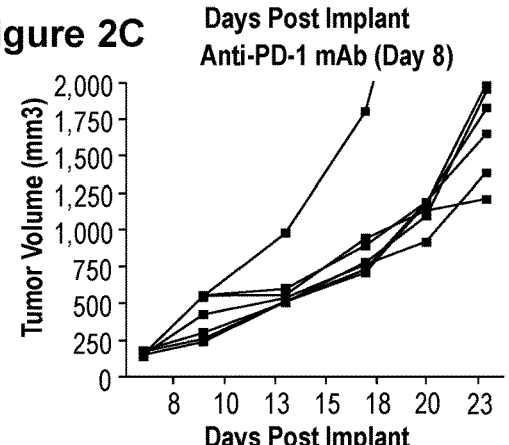
Anti-PD-1 mAb (Day 8)
Figure 2D
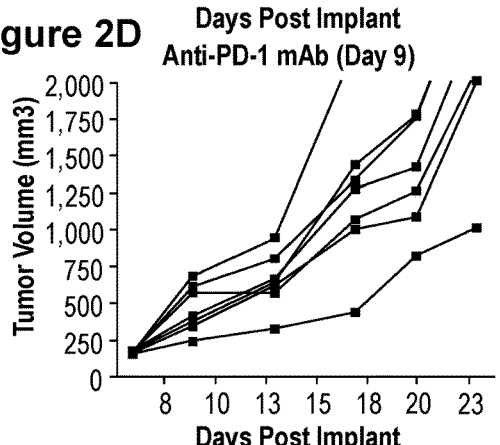
Anti-PD-1 mAb (Day 9)
Figure 2E
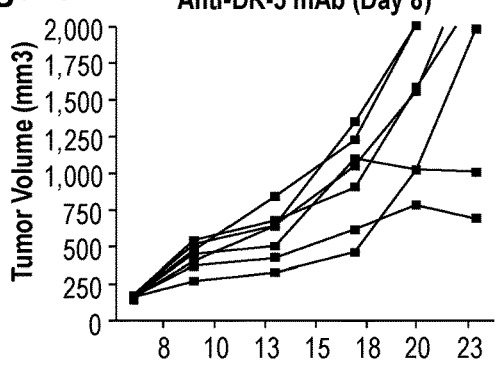
Anti-DR-5 mAb (Day 8)
Figure 2F
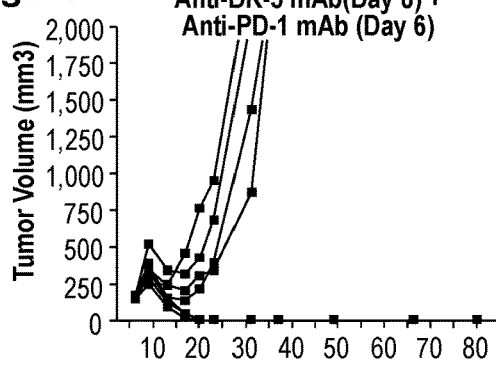
Anti-DR-5 mAb (Day 8) + Anti-PD-1 mAb (Day 6)
Figure 2G
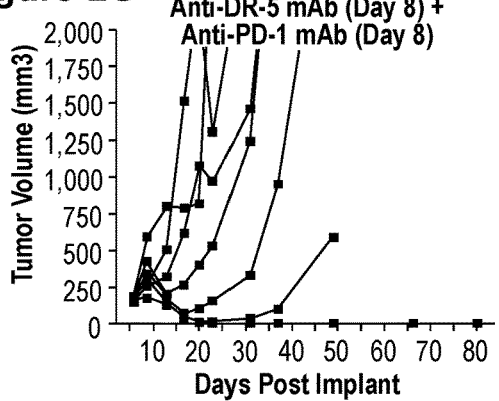
Anti-DR-5 mAb (Day 8) + Anti-PD-1 mAb (Day 8)
Figure 2H
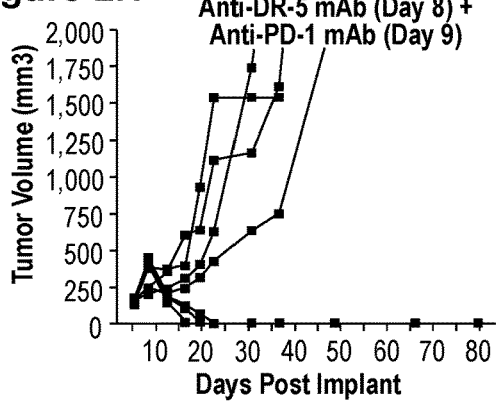
Anti-DR-5 mAb (Day 8) + Anti-PD-1 mAb (Day 9)
*Figure 2*

SEQUENCE LISTING

```
<160> NUMBER OF SEQ ID NOS: 27

<210> SEQ ID NO 1
<211> LENGTH: 123
<212> TYPE: PRT
<213> ORGANISM: Homo sapiens

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110
```

Trp Gly Gln Gly Thr Thr Val Thr Val Ser Ser
        115                 120

<210> SEQ ID NO 2
<211> LENGTH: 366
<212> TYPE: DNA
<213> ORGANISM: Homo sapiens

<400> SEQUENCE: 2
caggtccagc tggtgcagtc tggggctgag gtgaagaagc ctgggtcctc ggtgaaggtc     60
tcctgcaaga cttctggaga caccttcagc acctatgcta tcagctgggt gcgacaggcc    120
cctggacaag ggcttgagtg gatgggaggg atcatccctc tatttggtaa agcacactac    180
gcacagaagt tccagggcag agtcacgatt accgcggacg aatccacgag cacagcctac    240
atggagctga gcagcctgag atctgaggac acggccgtgt attttgtgc gagaaagttt     300 cactttgttt cggggagccc cttcggtatg gacgtctggg gccaagggac cacggtcacc    360
gtctcc                                                              366

<210> SEQ ID NO 3
<211> LENGTH: 106
<212> TYPE: PRT
<213> ORGANISM: Homo sapiens

<400> SEQUENCE: 3

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 4
<211> LENGTH: 318
<212> TYPE: DNA
<213> ORGANISM: Homo sapiens

<400> SEQUENCE: 4
gaaattgtgt tgacacagtc tccagccacc ctgtctttgt ctccagggga aagagccacc     60
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggccgacgtt cggccaaggg    300
accaaggtgg aaatcaaa                                                  318

<210> SEQ ID NO 5
<211> LENGTH: 5
<212> TYPE: PRT

```
<213> ORGANISM: Homo sapiens

<400> SEQUENCE: 5

Thr Tyr Ala Ile Ser
1               5

<210> SEQ ID NO 6
<211> LENGTH: 16
<212> TYPE: PRT
<213> ORGANISM: Homo sapiens

<400> SEQUENCE: 6

Gly Ile Ile Pro Ile Phe Gly Lys Ala His Tyr Ala Gln Lys Phe Gln
1               5                   10                  15

<210> SEQ ID NO 7
<211> LENGTH: 14
<212> TYPE: PRT
<213> ORGANISM: Homo sapiens

<400> SEQUENCE: 7

Lys Phe His Phe Val Ser Gly Ser Pro Phe Gly Met Asp Val
1               5                   10

<210> SEQ ID NO 8
<211> LENGTH: 11
<212> TYPE: PRT
<213> ORGANISM: Homo sapiens

<400> SEQUENCE: 8

Arg Ala Ser Gln Ser Val Ser Ser Tyr Leu Ala
1               5                   10

<210> SEQ ID NO 9
<211> LENGTH: 7
<212> TYPE: PRT
<213> ORGANISM: Homo sapiens

<400> SEQUENCE: 9

Asp Ala Ser Asn Arg Ala Thr
1               5

<210> SEQ ID NO 10
<211> LENGTH: 8
<212> TYPE: PRT
<213> ORGANISM: Homo sapiens

<400> SEQUENCE: 10

Gln Gln Arg Ser Asn Trp Pro Thr
1               5

<210> SEQ ID NO 11
<211> LENGTH: 440
<212> TYPE: PRT
<213> ORGANISM: Homo sapiens

<400> SEQUENCE: 11

Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45
```

```
Ala Val Ile Trp Tyr Asp Gly Ser Lys Arg Tyr Tyr Ala Asp Ser Val
 50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 12
<211> LENGTH: 214
<212> TYPE: PRT
```

<213> ORGANISM: Homo sapiens

<400> SEQUENCE: 12

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 13
<211> LENGTH: 113
<212> TYPE: PRT
<213> ORGANISM: Homo sapiens

<400> SEQUENCE: 13

```
Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser
```

<210> SEQ ID NO 14

<211> LENGTH: 339
<212> TYPE: DNA
<213> ORGANISM: Homo sapiens

<400> SEQUENCE: 14

```
caggtgcagc tggtggagtc tgggggaggc gtggtccagc ctgggaggtc cctgagactc      60
gactgtaaag cgtctggaat caccttcagt aactctggca tgcactgggt ccgccaggct     120
ccaggcaagg ggctggagtg ggtggcagtt atttggtatg atggaagtaa aagatactat     180
gcagactccg tgaagggccg attcaccatc tccagagaca attccaagaa cacgctgttt     240
ctgcaaatga acagcctgag agccgaggac acggctgtgt attactgtgc gacaaacgac     300
gactactggg gccagggaac cctggtcacc gtctcctca                            339
```

<210> SEQ ID NO 15
<211> LENGTH: 107
<212> TYPE: PRT
<213> ORGANISM: Homo sapiens

<400> SEQUENCE: 15

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Tyr
            20                  25                  30
Leu Ala Trp Tyr Gln Gln Lys Pro Gly Gln Ala Pro Arg Leu Leu Ile
        35                  40                  45
Tyr Asp Ala Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Ser Ser Asn Trp Pro Arg
                85                  90                  95
Thr Phe Gly Gln Gly Thr Lys Val Glu Ile Lys
            100                 105
```

<210> SEQ ID NO 16
<211> LENGTH: 321
<212> TYPE: DNA
<213> ORGANISM: Homo sapiens

<400> SEQUENCE: 16

```
gaaattgtgt tgacacagtc tccagccacc ctgtctttgt ctccagggga aagagccacc      60
ctctcctgca gggccagtca gagtgttagt agttacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag agtagcaact ggcctcggac gttcggccaa     300
gggaccaagg tggaaatcaa a                                               321
```

<210> SEQ ID NO 17
<211> LENGTH: 5
<212> TYPE: PRT
<213> ORGANISM: Homo sapiens

<400> SEQUENCE: 17

```
Asn Ser Gly Met His
1               5
```

```
<210> SEQ ID NO 18
<211> LENGTH: 17
<212> TYPE: PRT
<213> ORGANISM: Homo sapiens

<400> SEQUENCE: 18

Val Ile Trp Tyr Asp Gly Ser Lys Arg Tyr Tyr Ala Asp Ser Val Lys
1               5                   10                  15
Gly

<210> SEQ ID NO 19
<211> LENGTH: 4
<212> TYPE: PRT
<213> ORGANISM: Homo sapiens

<400> SEQUENCE: 19

Asn Asp Asp Tyr
1

<210> SEQ ID NO 20
<211> LENGTH: 11
<212> TYPE: PRT
<213> ORGANISM: Homo sapiens

<400> SEQUENCE: 20

Arg Ala Ser Gln Ser Val Ser Ser Tyr Leu Ala
1               5                   10

<210> SEQ ID NO 21
<211> LENGTH: 7
<212> TYPE: PRT
<213> ORGANISM: Homo sapiens

<400> SEQUENCE: 21

Asp Ala Ser Asn Arg Ala Thr
1               5

<210> SEQ ID NO 22
<211> LENGTH: 9
<212> TYPE: PRT
<213> ORGANISM: Homo sapiens

<400> SEQUENCE: 22

Gln Gln Ser Ser Asn Trp Pro Arg Thr
1               5

<210> SEQ ID NO 23
<211> LENGTH: 2106
<212> TYPE: DNA
<213> ORGANISM: Homo sapiens

<400> SEQUENCE: 23
agtttccctt ccgctcacct ccgcctgagc agtggagaag gcggcactct ggtggggctg      60
ctccaggcat gcagatccca caggcgccct ggccagtcgt ctgggcggtg ctacaactgg     120
gctggcggcc aggatggttc ttagactccc agacaggcc tggaaccccc ccaccttct      180 tcccagccct gctcgtggtg accgaagggg acaacgccac cttcacctgc agcttctcca     240
acacatcgga gagcttcgtg ctaaactggt accgcatgag ccccagcaac agacggaca      300 agctggccgc cttccccgag accgcagcc agcccggcca ggactgccgc ttccgtgtca     360
cacaactgcc caacgggcgt gacttccaca tgagcgtggt cagggcccgg cgcaatgaca     420
gcggcaccta cctctgtggg gccatctccc tggccccaa ggcgcagatc aaagagagcc     480
```

```
tgcgggcaga gctcaggtg acagagagaa gggcagaagt gcccacagcc caccccagcc      540
cctcacccag gccagccggc cagttccaaa ccctggtggt tggtgtcgtg gcggcctgc      600
tgggcagcct ggtgctgcta gtctgggtcc tggccgtcat ctgctcccgg gccgcacgag      660
ggacaatagg agccaggcgc accggccagc ccctgaagga ggacccctca gccgtgcctg      720
tgttctctgt ggactatggg gagctggatt ccagtggcg agagaagacc ccggagcccc       780
ccgtgccctg tgtccctgag cagacggagt atgccaccat tgtctttcct agcggaatgg      840
gcacctcatc cccgcccgc agggctcag ccgacggccc tcggagtgcc cagccactga       900
ggcctgagga tggacactgc tcttggcccc tctgaccggc ttccttggcc accagtgttc      960
tgcagaccct ccaccatgag cccgggtcag cgcatttcct caggagaagc aggcagggtg     1020
caggccattg caggccgtcc aggggctgag ctgcctgggg cgaccgggg ctccagcctg      1080
cacctgcacc aggcacagcc ccaccacagg actcatgtct caatgcccac agtgagccca     1140
ggcagcaggt gtcaccgtcc cctacaggga gggccagatg cagtcactgc ttcaggtcct     1200
gccagcacag agctgcctgc gtccagctcc ctgaatctct gctgctgctg ctgctgctgc     1260
tgctgctgcc tgcggcccgg ggctgaaggc gccgtggccc tgcctgacgc cccggagcct     1320
cctgcctgaa cttgggggct ggttggagat ggccttggag cagccaaggt gcccctggca     1380
gtggcatccc gaaacgccct ggacgcaggg cccaagactg gcacaggag tggaggtac      1440
atggggctgg ggactcccca ggagttatct gctccctgca ggcctagaga gtttcaggg     1500
aaggtcagaa gagctcctgg ctgtggtggg cagggcagga aacccctccc acctttacac     1560
atgcccaggc agcacctcag gcccttgtg gggcagggaa gctgaggcag taagcgggca     1620
ggcagagctg gaggcctttc aggccagcca gcactctggc ctcctgccgc cgcattccac     1680
cccagcccct cacaccactc gggagaggga catcctacgg tccaaggtc aggagggcag      1740
ggctggggtt gactcaggcc cctcccagct gtggccacct gggtgttggg agggcagaag     1800
tgcaggcacc tagggccccc catgtgccca ccctgggagc tctccttgga acccattcct     1860
gaaattattt aaaggggttg gccgggctcc caccagggcc tgggtgggaa ggtacaggcg     1920
ttcccccggg gcctagtacc cccgcgtggc ctatccactc ctcacatcca cacactgcac     1980
ccccactcct ggggcagggc caccagcatc caggcggcca gcaggcacct gagtggctgg     2040
gacaagggat cccccttccc tgtggttcta ttatattata attataatta aatatgagag     2100
catgct                                                                 2106
```

<210> SEQ ID NO 24
<211> LENGTH: 290
<212> TYPE: PRT
<213> ORGANISM: Homo sapiens

<400> SEQUENCE: 24

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

```
Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
290

<210> SEQ ID NO 25
<211> LENGTH: 176
<212> TYPE: PRT
<213> ORGANISM: Homo sapiens

<400> SEQUENCE: 25

Met Arg Ile Phe Ala Val Phe Ile Phe Met Thr Tyr Trp His Leu Leu
1               5                   10                  15

Asn Ala Pro Tyr Asn Lys Ile Asn Gln Arg Ile Leu Val Val Asp Pro
                20                  25                  30

Val Thr Ser Glu His Glu Leu Thr Cys Gln Ala Glu Gly Tyr Pro Lys
            35                  40                  45

Ala Glu Val Ile Trp Thr Ser Ser Asp His Gln Val Leu Ser Gly Lys
    50                  55                  60

Thr Thr Thr Thr Asn Ser Lys Arg Glu Glu Lys Leu Phe Asn Val Thr
65                  70                  75                  80

Ser Thr Leu Arg Ile Asn Thr Thr Thr Asn Glu Ile Phe Tyr Cys Thr
                85                  90                  95

Phe Arg Arg Leu Asp Pro Glu Glu Asn His Thr Ala Glu Leu Val Ile
            100                 105                 110

Pro Glu Leu Pro Leu Ala His Pro Pro Asn Glu Arg Thr His Leu Val
        115                 120                 125

Ile Leu Gly Ala Ile Leu Leu Cys Leu Gly Val Ala Leu Thr Phe Ile
    130                 135                 140

Phe Arg Leu Arg Lys Gly Arg Met Met Asp Val Lys Lys Cys Gly Ile
```

-continued

```
               145                 150                 155                 160
Gln Asp Thr Asn Ser Lys Lys Gln Ser Asp Thr His Leu Glu Glu Thr
                165                 170                 175

<210> SEQ ID NO 26
<211> LENGTH: 411
<212> TYPE: PRT
<213> ORGANISM: Homo sapiens

<400> SEQUENCE: 26

Met Glu Gln Arg Gly Gln Asn Ala Pro Ala Ser Gly Ala Arg Lys
1               5                   10                  15

Arg His Gly Pro Gly Pro Arg Glu Ala Arg Gly Ala Arg Pro Gly Leu
                20                  25                  30

Arg Val Pro Lys Thr Leu Val Leu Val Val Ala Ala Val Leu Leu Leu
                35                  40                  45

Val Ser Ala Glu Ser Ala Leu Ile Thr Gln Gln Asp Leu Ala Pro Gln
        50                  55                  60

Gln Arg Val Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
                100                 105                 110

Cys Leu Arg Cys Thr Arg Cys Asp Ser Gly Glu Val Glu Leu Ser Pro
            115                 120                 125

Cys Thr Thr Thr Arg Asn Thr Val Cys Gln Cys Glu Glu Gly Thr Phe
    130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Ile Ile Gly Val Thr Val Ala
                180                 185                 190

Ala Val Val Leu Ile Val Ala Val Phe Val Cys Lys Ser Leu Leu Trp
            195                 200                 205

Lys Lys Val Leu Pro Tyr Leu Lys Gly Ile Cys Ser Gly Gly Gly Gly
    210                 215                 220

Asp Pro Glu Arg Val Asp Arg Ser Ser Gln Arg Pro Gly Ala Glu Asp
225                 230                 235                 240

Asn Val Leu Asn Glu Ile Val Ser Ile Leu Gln Pro Thr Gln Val Pro
                245                 250                 255

Glu Gln Glu Met Glu Val Gln Glu Pro Ala Glu Pro Thr Gly Val Asn
                260                 265                 270

Met Leu Ser Pro Gly Glu Ser Glu His Leu Leu Glu Pro Ala Glu Ala
            275                 280                 285

Glu Arg Ser Gln Arg Arg Arg Leu Leu Val Pro Ala Asn Glu Gly Asp
    290                 295                 300

Pro Thr Glu Thr Leu Arg Gln Cys Phe Asp Asp Phe Ala Asp Leu Val
305                 310                 315                 320

Pro Phe Asp Ser Trp Glu Pro Leu Met Arg Lys Leu Gly Leu Met Asp
                325                 330                 335

Asn Glu Ile Lys Val Ala Lys Ala Glu Ala Ala Gly His Arg Asp Thr
                340                 345                 350
```

```
Leu Tyr Thr Met Leu Ile Lys Trp Val Asn Lys Thr Gly Arg Asp Ala
            355                 360                 365

Ser Val His Thr Leu Leu Asp Ala Leu Glu Thr Leu Gly Glu Arg Leu
    370                 375                 380

Ala Lys Gln Lys Ile Glu Asp His Leu Leu Ser Ser Gly Lys Phe Met
385                 390                 395                 400

Tyr Leu Glu Gly Asn Ala Asp Ser Ala Met Ser
                405                 410

<210> SEQ ID NO 27
<211> LENGTH: 6
<212> TYPE: PRT
<213> ORGANISM: Unknown
<220> FEATURE:
<223> OTHER INFORMATION: Description of Unknown: CTLA-4 motif
      peptide

<400> SEQUENCE: 27

Met Tyr Pro Pro Pro Tyr
1               5
```

COMBINATION OF DR5 AGONIST AND ANTI-PD-1 ANTAGONIST AND METHODS OF USE

CROSS-REFERENCE TO RELATED APPLICATIONS

This application is a continuation of U.S. patent application Ser. No. 14/774,382, filed on Sep. 10, 2015, now pending, which application is a U.S. National Stage Entry of International Application No. PCT/US2014/024208, filed Mar. 12, 2014, which claims the benefit of U.S. Provisional Application No. 61/783,184, filed on Mar. 14, 2013. The entire contents of these applications are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on May 10, 2018, is named "MXI-529US-CN_Sequence-Listing.txt" and is 24884 Kilobytes in size. The Sequence Listing is being submitted by EFS Web and is hereby incorporated by reference into the specification.

BACKGROUND

The National Cancer Institute has estimated that in the United States alone, 1 in 3 people will be struck with cancer during their lifetime. Moreover, approximately 50% to 60% of people contracting cancer will eventually succumb to the disease. The widespread occurrence of this disease underscores the need for improved anticancer regimens for the treatment of malignancy.

Programmed Cell Death 1 (PD-1) is a cell surface signaling receptor that plays a critical role in the regulation of T cell activation and tolerance (Keir M E, et al., *Annu Rev Immunol* 2008; 26:677-704). It is a type I transmembrane protein and together with BTLA, CTLA-4, ICOS and CD28, comprise the CD28 family of T cell co-stimulatory receptors. PD-1 is primarily expressed on activated T cells, B cells, and myeloid cells (Dong H, et al., *Nat Med* 1999; 5:1365-1369). It is also expressed on natural killer (NK) cells (Terme M, et al., *Cancer Res* 2011; 71:5393-5399). PD-1 is highly expressed on tumor infiltrating lymphocytes, and its ligands are up-regulated on the cell surface of many different tumors (Dong H, et al., *Nat Med* 2002; 8:793-800). Multiple murine cancer models have demonstrated that binding of ligand to PD-1 results in immune evasion. In addition, blockade of this interaction results in anti-tumor activity.

Two cell surface glycoprotein ligands for PD-1 have been identified, PD-L1 and PD-L2, and have been shown to downregulate T cell activation and cytokine secretion upon binding to PD-1 (Freeman et al. (2000) J Exp Med 192: 1027-34; Latchman et al. (2001) Nat Immunol 2:261-8; Carter et al. (2002) Eur J Immunol 32:634-43; Ohigashi et al. (2005) Clin Cancer Res 11:2947-53). Both PD-L1 (B7-H1) and PD-L2 (B7-DC) are B7 homologs that bind to PD-1, but do not bind to other CD28 family members (Blank et al. (2004). Expression of PD-L1 on the cell surface has also been shown to be upregulated through IFN-gamma stimulation.

PD-L1 expression has been found in several murine and human cancers, including human lung, ovarian and colon carcinoma and various myelomas (Iwai et al. (2002) PNAS 99:12293-7; Ohigashi et al. (2005) Clin Cancer Res 11:2947-53). PD-L1 has been suggested to play a role in tumor immunity by increasing apoptosis of antigen-specific T-cell clones (Dong et al. (2002) Nat Med 8:793-800). It has also been suggested that PD-L1 might be involved in intestinal mucosal inflammation and inhibition of PD-L1 suppresses wasting disease associated with colitis (Kanai et al. (2003) J Immunol 171:4156-63).

TRAIL (tumor necrosis factor (TNF)-related apoptosis-inducing ligand) is a member of the TNF superfamily with the ability to induce apoptosis of tumor cells. At least five receptors for TRAIL have been identified. DR4 (TRAIL-R1) and DR5 (TRAIL-R2) are apoptosis-inducing receptors, which each contain an intracellular death domain (see e.g., Pan G, et al., Science. 1997;276:111-113, Pan G, et al., Science. 1997; 277:815-818, Sheridan JP, et al., Science. 1997;277:818-821, and Walczak H, et al., EMBO J. 1997; 16:5386-5397). Upon receptor activation, DR4 and DR5 recruit FAS associated protein with death domain (FADD) and caspase-8 to form the death-inducing signaling complex (DISC), which activates caspase-8, subsequently leading to the activation of executioner caspases such as caspase-3 that induce apoptosis (see, e.g., Kischkel F C, et al., Immunity. 2000;12:611-620, Thomas L R, et al., J Biol Chem. 2004; 279:32780-32785, Thomas L R, et al., J Biol Chem. 2004; 279:52479-52486, Varfolomeev E, et al., J Biol Chem. 2005; 280:40599-40608, Ashkenazi A., Nat Rev Cancer. 2002; 2:420-430, and Thorburn A. Cell Signal. 2004; 16:139-144).

TRAIL and agonistic antibodies that recognize TRAIL receptors preferentially kill tumor cells and induce potent anti-tumor activity in a variety of experimental models (see, Griffith T S, et al., Curr Opin Immunol. 1998; 10:559-563, Ashkenazi A, et al., J Clin Invest. 1999; 104:155-162, Walczak H, et al, Nat Med. 1999; 5:157-163, Chuntharapai A, et al., J Immunol. 2001; 166:4891-4898, and Ichikawa K, et al., Nat Med. 2001;7:954-960). Administration of TRAIL to mice bearing human tumors actively suppressed tumor progression and improved survival of the animal (Walczak H, et al, Nat Med. 1999; 5:157-163). Accordingly, agonists against DR4 or DR5 by activating apoptosis are becoming dramatically meaningful as candidates for the treatment of cancer.

SUMMARY OF THE INVENTION

The present inventors have discovered for the first time that co-administration of a DR5 agonist (e.g., an antibody) and an anti-PD-1 antagonist (e.g., an antibody) effectively inhibits tumor growth in vivo, even synergistically. Accordingly, it is an object of the present invention to provide improved methods for treating subjects with cancer. Specifically, it is an object of the invention to provide efficacious combination treatment regimens wherein a DR5 agonist is combined with an anti-PD-1 antagonist for the treatment of cancer.

The present invention provides a method for the treatment of cancer in a subject by co-administering an effective amount of a PD-1 antagonist and an agent that induces apoptosis in cancer cells, e.g., an agent that engages the DR4 or DR5 receptor, such as a DR4 or DR5 agonist.

Suitable anti-DR5 agonists for use in the methods of the invention, include, without limitation, ligands, antibodies (e.g., monoclonal antibodies and bispecific antibodies) and multivalent agents. In one embodiment, the DR5 agonist is an antibody selected from the group consisting of Lexatumumab (also known as ETR2-ST01), Tigatuzumab (also known as CS-1008), Conatumumab (also known as AMG 655), Drozitumab, HGSTR2J/KMTRS, and LBY-135. In another embodiment, the DR5 agonist is a multivalent agent (e.g., TAS266). In a further embodiment, the DR5 agonist is a ligand (e.g., a TNF-related apoptosis-inducing ligand (TRAIL), such as a recombinant human TRAIL, e.g., Dulanermin (also known as AMG951)).

Suitable PD-1 antagonists for use in the methods of the invention, include, without limitation, ligands, antibodies (e.g., monoclonal antibodies and bispecific antibodies), and multivalent agents. In one embodiment, the PD-1 antagonist is a fusion protein, e.g., an Fc fusion protein, such as AMP-244. In one embodiment, the PD-1 antagonist is an anti-PD-1 or anti-PD-L1 antibody. In another embodiment, the PD-1 antagonist is an antibody, such as MK-3475 or CT-011.

An exemplary anti-PD-1 antibody is 5C4 (referred to as 5C4 in WO 2006/121168; also known as MDX-1106, ONO-4538, and Nivolumab) comprising heavy and light chains having the sequences shown in SEQ ID NOs: 11 and 12, respectively, or antigen binding fragments and variants thereof. In other embodiments, the antibody comprises the heavy and light chain CDRs or VRs of 5C4. Accordingly, in one embodiment, the antibody comprises the CDR1, CDR2, and CDR3 domains of the VH region of 5C4 having the sequence shown in SEQ ID NO: 13, and the CDR1, CDR2 and CDR3 domains of the VL region of 5C4 having the sequence shown in SEQ ID NO:15. In another embodiment, the antibody comprises the heavy chain CDR1, CDR2 and CDR3 domains having the sequences set forth in SEQ ID NOs: 17, 18, and 19, respectively, and the light chain CDR1, CDR2 and CDR3 domains having the sequences set forth in SEQ ID NOs: 20, 21, and 22, respectively. In another embodiment, the antibody comprises VH and/or VL regions having the amino acid sequences set forth in SEQ ID NO: 13 and/or SEQ ID NO: 15, respectively. In another embodiment, the antibody comprises the heavy chain variable (VH) and/or light chain variable (VL) regions encoded by the nucleic acid sequences set forth in SEQ ID NO: 14 and/or SEQ ID NO: 16, respectively. In another embodiment, the antibody competes for binding with, and/or binds to the same epitope on PD-1 as, the above-mentioned antibodies. In another embodiment, the antibody has at least about 90% variable region amino acid sequence identity with the above-mentioned antibodies (e.g., at least about 90%, 95% or 99% variable region identity with SEQ ID NO: 13 or SEQ ID NO: 15).

In one embodiment, the PD-1 antagonist is an anti-PD-L1 antibody, such as MEDI4736 (also known as Anti-B7-H1) or MPDL3280A (also known as RG7446). An exemplary anti-PD-L1 antibody is 12A4 (referred to as 12A4 in WO 2007/005874 and U.S. Pat. No. 7,943,743). In one embodiment, the antibody comprises the heavy and light chain CDRs or VRs of 12A4. Accordingly, in one embodiment, the antibody comprises the CDR1, CDR2, and CDR3 domains of the VH region of 12A4 having the sequence shown in SEQ ID NO: 1, and the CDR1, CDR2 and CDR3 domains of the VL region of 5C4 having the sequence shown in SEQ ID NO: 3. In another embodiment, the antibody comprises the heavy chain CDR1, CDR2 and CDR3 domains having the sequences set forth in SEQ ID NOs: 5, 6, and 7, respectively, and the light chain CDR1, CDR2 and CDR3 domains having the sequences set forth in SEQ ID NOs: 8, 9, and 10, respectively. In another embodiment, the antibody comprises VH and/or VL regions having the amino acid sequences set forth in SEQ ID NO: 1and/or SEQ ID NO: 3, respectively. In another embodiment, the antibody comprises the heavy chain variable (VH) and/or light chain variable (VL) regions encoded by the nucleic acid sequences set forth in SEQ ID NO: 2 and/or SEQ ID NO: 4, respectively. In another embodiment, the antibody competes for binding with, and/or binds to the same epitope on PD-L1 as, the above-mentioned antibodies. In another embodiment, the antibody has at least about 90% variable region amino acid sequence identity with the above-mentioned antibodies (e.g., at least about 90%, 95% or 99% variable region identity with SEQ ID NO: 1 or SEQ ID NO: 3).

In one embodiment, the invention provides a method of treating cancer in a subject, the method comprising administering to the subject an effective amount of a PD-1 antagonist and a DR5 agonist, wherein
(a) the PD-1 antagonist is an anti-PD-1 antibody comprising the CDR1, CDR2 and CDR3 domains in a heavy chain variable region having the sequence set forth in SEQ ID NO: 13, and the CDR1, CDR2 and CDR3 domains in a light chain variable region having the sequence set forth in SEQ ID NO: 15; and
(b) the DR5 agonist is an antibody.

In another embodiment, the invention provides a method cancer in a subject, the method comprising administering to the subject an effective amount of a PD-1 antagonist and a DR5 agonist, wherein
(a) the PD-1 antagonist is an anti-PD-L1 antibody comprising the CDR1, CDR2 and CDR3 domains in a heavy chain variable region having the sequence set forth in SEQ ID NO: 1, and the CDR1, CDR2 and CDR3 domains in a light chain variable region having the sequence set forth in SEQ ID NO: 3; and
(b) the DR5 agonist is an antibody.

The efficacy of the treatment methods provided herein can be assessed using any suitable means. In one embodiment, the treatment produces at least one therapeutic effect selected from the group consisting of reduction in size of a tumor, reduction in number of metastasic lesions over time, complete response, partial response, and stable disease. In another embodiment, administration of a PD-1 antagonist and a DR5 agonist results in at least a 1, 1.25, 1.50, 1.75, 2, 2.25, 2.50, 2.75, 3, 3.25, 3.5, 3.75, or 4-fold reduction in tumor volume, e.g., relative to treatment with the PD-1 antagonist or DR5 agonist alone, or relative to tumor volume before initiation of treatment. In another embodiment, administration of the PD-1 antagonist and DR5 agonist results in at least a 1-fold, 2-fold, or more preferably a 3-fold reduction in tumor volume, e.g., relative to treatment with the PD-1 antagonist or DR5 agonist alone, or relative to tumor volume before initiation of treatment. In a further embodiment, administration of a PD-1 antagonist and a DR5 agonist results in tumor growth inhibition of at least 50%, 60%, 70% or 80%, e.g., relative to treatment with the PD-1 antagonist or DR5 agonist alone, or relative to tumor volume before initiation of treatment. In certain embodiments, tumor volume is reduced by 50%, 60%, 70%, 80%, 90% or more, e.g., relative to tumor size before initiation of the treatment.

The PD-1 antagonist and DR5 agonist can be administered accordingly to a suitable dosage, route (e.g., intravenous, intraperitoneal, intramuscular, intrathecal or subcutaneous). The antagonist and agonist can also be administered according to any suitable schedule. For example, the antagonist and agonist can be simultaneously administered in a single formulation. Alternatively, the antagonist and agonist can be formulated for separate administration, wherein they are administered concurrently or sequentially. In one embodiment, the PD-1 antagonist is administered prior to administration of the DR5 agonist. In another embodiment, the DR5 agonist is administered prior to administration of the PD-1 antagonist. In a further embodiment, the DR5 agonist and the PD-1 antagonist are administered simultaneously.

In one embodiment, the cancer is a cancer selected from the group consisting of leukemia, lymphoma, blastoma, carcinoma and sarcoma. In another embodiment, the cancer is selected from the group consisting of chronic myeloid leukemia, acute lymphoblastic leukemia, Philadelphia chromosome positive acute lymphoblastic leukemia (Ph+ ALL), squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, pediatric sarcoma, sinonasal natural killer, multiple myeloma, acute myelogenous leukemia (AML), and chronic lymphocytic leukemia (CIVIL).

Additional agents and therapies can be administered in combination with the agonists and antagonists described herein. In one embodiment, the methods comprise administration of an additional therapeutic agent (e.g., a cyotoxin or chemotherapeutic agent.

Also provided herein are compositions comprising a PD-1 antagonist and a DR5 agonist. In one embodiment, the antagonist and/or agonist is a ligand, antibody (e.g., monoclonal antibody or bispecific antibody) or multivalent agent. In another embodiment, the PD-1 antagonist is an anti-PD-1 antibody comprising the heavy and light chain CDRs or VRs of 5C4. In another embodiment, the PD-1 antagonist is an anti-PD-L1 antibody comprising the heavy and light chain CDRs or VRs of 12A4.

Further provided are kits for treating a cancer in a subject, the kit comprising:

(a) a dose of a PD-1 antagonist;
(b) a dose of a DR5 agonist; and
(c) instructions for using the PD-1 antagonist and DR5 agonist in the methods described herein. In one embodiment, the DR5 agonist is an antibody. In another embodiment, the PD-1 antagonist is an antibody. In particular embodiment, the PD-1 antagonist is an anti-PD-1 antibody comprising the CDR1, CDR2 and CDR3 domains in a heavy chain variable region having the sequence set forth in SEQ ID NO: 13, and the CDR1, CDR2 and CDR3 domains in a light chain variable region having the sequence set forth in SEQ ID NO: 15. In another particular embodiment, the PD-1 antagonist is an anti-PD-L1 antibody comprising antibody comprises the CDR1, CDR2 and CDR3 domains in a heavy chain variable region having the sequence set forth in SEQ ID NO: 1, and the CDR1, CDR2 and CDR3 domains in a light chain variable region having the sequence set forth in SEQ ID NO: 3.

BRIEF DESCRIPTION OF THE DRAWINGS

FIGS. 2A-2H depict the tumor volume in individual mice administered a control (FIG. 2A), an anti-PD-1 antibody on day 6 post-implant (FIG. 2B), an anti-PD-1 antibody on day 8 post-implant (FIG. 2C), an anti-PD-1 antibody on day 9 post-implant (FIG. 2D), an anti-DR5 antibody on day 8 post-implant (FIG. 2E), an anti-DR5 antibody on day 8 post-implant in combination with an anti-PD-1 antibody on day 6 post-implant (FIG. 2F), an anti-DR5 antibody on day 8 post-implant in combination with an anti-PD-1 antibody on day 8 post-implant (FIG. 2G), and an anti-DR5 antibody on day 8 post-implant in combination with an anti-PD-1 antibody on day 9 post-implant (FIG. 2H).

DETAILED DESCRIPTION OF THE INVENTION

Figure 1:
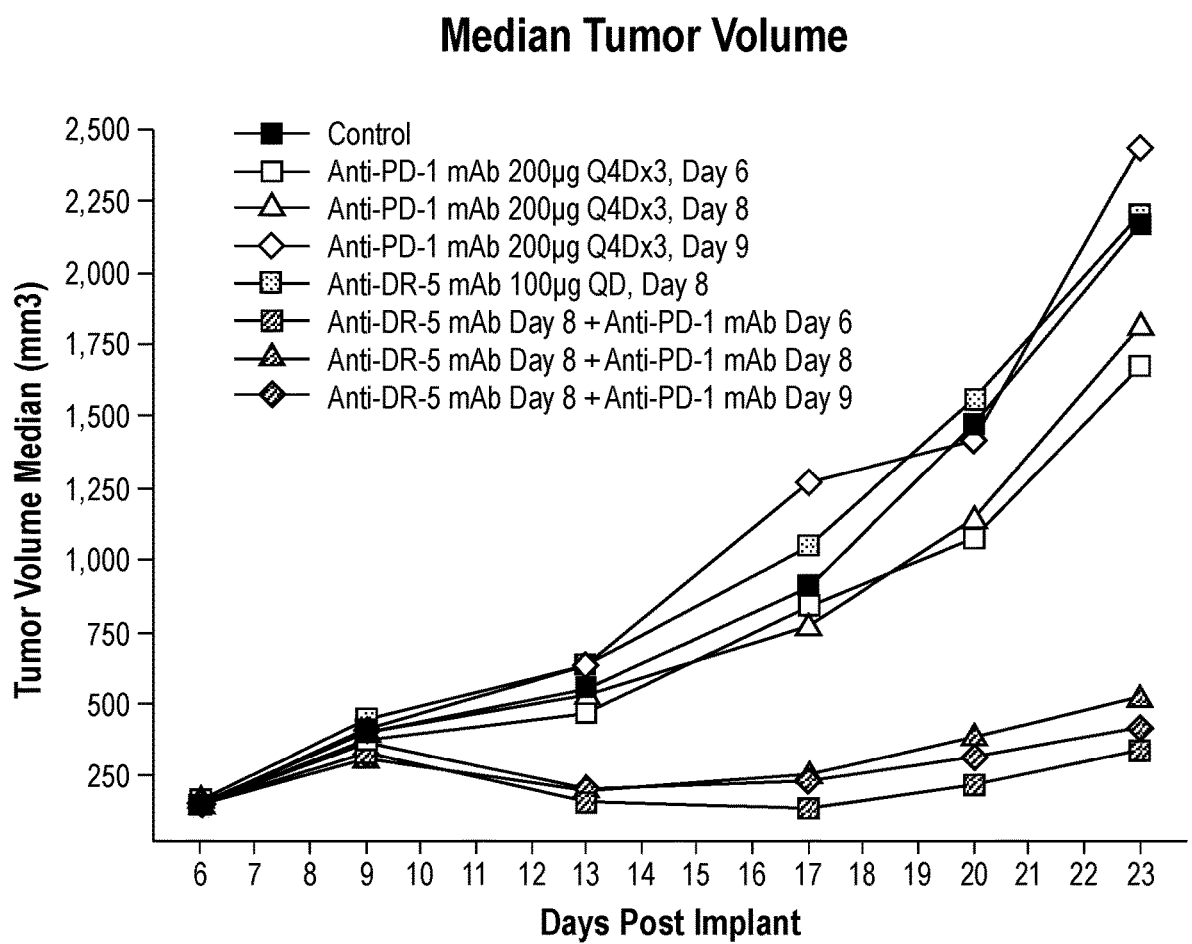
FIG. 1 is a graph depicting the median tumor volume in mice (mm$^3$) after administration of a control, an anti-DR5 antibody, an anti-PD-1 antibody, or combination of both an anti-DR5 antibody, an anti-PD-1 antibody, up to 23 days post implant.

As described herein, the invention is based on the discovery that co-administration of a DR5 agonist (e.g., an antibody) and a PD-1 antagonist (e.g., an antibody) effectively inhibits tumor growth in vivo, even synergistically. Accordingly, the present invention provides a method for the treatment of cancer in a subject which comprises administering to a subject (e.g., human) an effective amount of a PD-1 antagonist and a DR5 agonist.

I. Definitions

Unless defined otherwise, all technical and scientific terms used herein have the same meaning as commonly understood by the skilled artisan. Although any methods and compositions similar or equivalent to those described herein can be used in practice or testing of the present invention, the preferred methods and compositions are described herein.

As used herein, the term "subject" or "patient" is a human patient (e.g., a patient having cancer).

A "solid tumor" includes, for example, sarcoma, melanoma, carcinoma, prostate carcinoma, lung carcinoma, colon carcinoma, or other solid tumor cancer.

The terms "cancer", "cancerous", or "malignant" refer to or describe the physiological condition in mammals that is typically characterized by unregulated cell growth. Examples of cancer include, for example, leukemia, lymphoma, blastoma, carcinoma and sarcoma. More particular examples of such cancers include chronic myeloid leukemia, acute lymphoblastic leukemia, Philadelphia chromosome positive acute lymphoblastic leukemia (Ph+ALL), squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, pediatric sarcoma, sinonasal natural killer, multiple myeloma, acute myelogenous leukemia (AML), and chronic lymphocytic leukemia (CML).

As used herein, "effective treatment" refers to treatment producing a beneficial effect, e.g., amelioration of at least one symptom of a disease or disorder. A beneficial effect can take the form of an improvement over baseline, i.e., an improvement over a measurement or observation made prior to initiation of therapy according to the method. A beneficial effect can also take the form of arresting, slowing, retarding, or stabilizing of a deleterious progression of a marker of cancer. Effective treatment may refer to alleviation of at least one symptom of cancer. Such effective treatment may, e.g., reduce patient pain, reduce the size and/or number of lesions, may reduce or prevent metastasis of a tumor, and/or may slow tumor growth.

term "effective amount" refers to an amount of an agent that provides the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In reference to solid tumors, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay tumor development. In some embodiments, an effective amount is an amount sufficient to prevent or delay tumor recurrence. An effective amount can be administered in one or more administrations. The effective amount of the drug or composition may: (i) reduce the number of cancer cells; (ii) reduce tumor size; (iii) inhibit, retard, slow to some extent and may stop cancer cell infiltration into peripheral organs; (iv) inhibit (i.e., slow to some extent and may stop tumor metastasis; (v) inhibit tumor growth; (vi) prevent or delay occurrence and/or recurrence of tumor; and/or (vii) relieve to some extent one or more of the symptoms associated with the cancer. In one example, an "effective amount" is the amount of a PD-1 antagonist (e.g., an antibody) and DR5 agonist antibody (e.g., an antibody), in combination, to effect a significant decrease in cancer or slowing of progression of cancer, such as an advanced solid tumor.

As used herein, the term "antagonist" refers to a molecule which blocks (e.g., reduces or prevents) a biological activity.

As used herein, the term "agonist" refers to a molecule that triggers (e.g., initiates or promotes), partially or fully enhances, stimulates or activates one or more biological activities. Agonists often mimic the action of a naturally occurring substance. Whereas an agonist causes an action, an antagonist blocks the action of the agonist.

As used herein, the term "ligand" refers to a molecule that forms a complex with a biomolecule (e.g., a receptor) to serve a biological purpose. In a narrower sense, is a signal triggering molecule, binding to a site on a target protein. The binding occurs by intermolecular forces, such as ionic bonds, hydrogen bonds and van der Waals forces. The docking (association) is usually reversible (dissociation). Actual irreversible covalent binding between a ligand and its target molecule is rare in biological systems. Ligand binding to a receptor (receptor protein) alters its chemical conformation (three dimensional shape). The conformational state of a receptor protein determines its functional state.

As used herein, the terms "synergy", "therapeutic synergy", and "synergistic effect" refer to a phenomenon where treatment of patients with a combination of therapeutic agents (e.g., PD-1 antagonist in combination with DR5 agonist) manifests a therapeutically superior outcome to the outcome achieved by each individual constituent of the combination used at its optimum dose (see, e.g., T. H. Corbett et al., 1982, *Cancer Treatment Reports*, 66, 1187). In this context a therapeutically superior outcome is one in which the patients either a) exhibit fewer incidences of adverse events while receiving a therapeutic benefit that is equal to or greater than that where individual constituents of the combination are each administered as monotherapy at the same dose as in the combination, or b) do not exhibit dose-limiting toxicities while receiving a therapeutic benefit that is greater than that of treatment with each individual constituent of the combination when each constituent is administered in at the same doses in the combination(s) as is administered as individual components. In xenograft models, a combination, used at its maximum tolerated dose, in which each of the constituents will be present at a dose generally not exceeding its individual maximum tolerated dose, manifests therapeutic synergy when decrease in tumor growth achieved by administration of the combination is greater than the value of the decrease in tumor growth of the best constituent when the constituent is administered alone.

As used herein, the term "antibody" includes whole antibodies and any antigen binding fragment (i.e., "antigen-binding fragments" (also known as "antigen-binding portions")) or single chains thereof. Whole antibodies are glycoproteins comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, $C_H1$, $C_H2$ and $C_H3$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system. The term "antibody" also encompasses chimeric antibodies, humanized antibodies, fully human antibodies, as well as multimeric forms of antibodies, such as minibodies, bis-scFv, diabodies, triabodies, tetrabodies and chemically conjugated Fab' multimers.

The term "antibody fragment" (also referred to as "antigen-binding fragment" or "antigen-binding portion"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the $V_L$, $V_H$, $C_L$ and $C_H1$ domains; (ii) a F(ab')$_2$ fragment, a bivalent fragment is essentially a Fab with part of the hinge region (see, FUNDAMENTAL IMMUNOLOGY (Paul ed., 3.sup.rd ed. 1993); (iv) a Fd fragment consisting of the $V_H$ and $C_H1$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody (also known as a single-domain antibody (sdAb)), which is a heavy chain variable region containing a single variable domain and two constant domains. Single domain antibodies include $V_H$H fragments (single-domain antibodies engineered from heavy-chain antibodies found in camelids, as well as VNAR fragments (single-domain antibodies obtained from heavy-chain antibodies (IgNAR, 'immunoglobulin new antigen receptor') of cartilaginous fishes).

"Antigen binding scaffolds" are proteins that bind specifically to a target (or antigen) or epitope , such as proteins comprising an Ig fold or an Ig-like fold, e.g., the DR5 binding proteins described in WO2009/058379 and WO2011/130328, Antibodies or antigen binding fragments thereof are also antigen binding scaffolds. Antigen binding scaffolds can be monovalent, multivalent, e.g., bivalent, trivalent, tetravalent, or bind 5, 6 or more epitopes. Multivalent antigen binding scaffolds can be monospecific or multispecific, i.e., binding to multiple (at least 2, 3, 4 or 5) epitopes that are different from one another. For example, a multivalent monospecific antigen binding scaffold is a protein that binds to at least 2, 3, 4 or 5 identical epitopes, and may be a protein comprising at least 2, 3, 4 or 5 identical antigen binding portions. For example, DR5 binding scaffolds may comprise 2-10, e.g., 2-6, 2-5, 2-4 or 2-3 DR5 binding portions, which may be the same or different from one another.

A multivalent antibody includes antibodies comprising at least 2, 3, 4, 5, 6, 7, 8, 9, 10 or more antigen binding portions of antibodies, which antigen binding portions may comprise a portion of a heavy chain and a portion of a light chain. An antigen binding portion may be on a single polypeptide or comprise more than one polypeptide. For example, a multivalent antibody may comprise from 2-10 antigen binding portions, which may be the same or different from each other. A multivalent antibody may be monospecific or multispecific. A multispecific antibody may be bispecific, trispecific, tetraspecific or bind to 5 or more different epitopes.

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies.

As used herein, an antigen binding scaffold that "specifically binds" to an antigen or epitope thereof is an antigen binding scaffold that binds to the antigen or epitope thereof with a $K_D$ of $10^{-7}$ M, $5\times10^{-8}$ M, $10^{-8}$ M, $5\times10^{-9}$M, $10^{-9}$M, $5\times10^{-10}$ M, $10^{-10}$ M, $5\times10^{-11}$ M, $10^{-11}$ M, $5\times10^{-12}$ M, $10^{-12}$M or less. For example, an antigen binding scaffold that specifically binds to DR5 is an antigen binding scaffold that binds to DR5 with a $K_D$ of $10^{-7}$ M, $5\times10^{-8}$M, $10^{-8}$ M, $5\times10^{-9}$M, $10^{-9}$ M, $5\times10^{-10}$ M, $10^{-10}$ M, $5\times10^{-11}$ M, $10^{-11}$ M, $5\times10^{-12}$ M, $10^{-12}$ M or less. For example, an antibody that "specifically binds to human PD-1" or "specifically binds to human PD-L1" is intended to refer to an antibody that binds to human PD-1 or PD-L1, respectively, with a $K_D$ of $10^{-7}$ M, $5\times10^{-8}$ M, $10^{-8}$ M, $5\times10^{-9}$ M, $10^{-9}$M, $5\times10^{-10}$ M, $10^{-10}$ M, $5\times10^{-11}$M, $10^{-11}$ M, $5\times10^{-12}$M, $10^{-12}$ M or less. An antigen binding scaffold that comprises 2 or more regions binding to an antigen or epitope may bind specifically to the antigen or epitope even it has a lower affinity of binding to the antigen or epitope than the ranges provided above, as it will bind to the antigen or epitope with increased avidity.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Song-sivilai & Lachmann, *Clin. Exp. Immunol.* 79:315-321 (1990); Kostelny et al., *J. Immunol.* 148, 1547-1553 (1992).

The term "monoclonal antibody" or "monoclonal antibody composition," as used herein, refers to an antibody or a composition of antibodies that displays a single binding specificity and affinity for a particular epitope. Accordingly, the term "human monoclonal antibody" or "monoclonal antibody composition" refers to an antibody or a composition of antibodies which displays a single binding specificity and which has variable and optional constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art and those described herein, for example, x-ray crystallography and 2-dimensional nuclear magnetic resonance (see, e.g., *Epitope Mapping Protocols in Methods in Molecular Biology*, Vol. 66, G. E. Morris, Ed. (1996)).

The term "epitope mapping" refers to the process of identification of the molecular determinants for antibody-antigen recognition.

The term "binds to the same epitope," with reference to two or more antibodies, means that the antibodies compete for binding to an antigen and bind to the same, overlapping, or encompassing continuous or discontinuous segments of amino acids. Those of skill in the art understand that the phrase "binds to the same epitope" does not necessarily mean that the antibodies bind to exactly the same amino acids. The precise amino acids to which the antibodies bind can differ. For example, a first antibody can bind to a segment of amino acids that is completely encompassed by the segment of amino acids bound by a second antibody. In another example, a first antibody binds one or more segments of amino acids that significantly overlap the one or more segments bound by the second antibody. For the purposes herein, such antibodies are considered to "bind to the same epitope."

Accordingly, also, encompassed by the present invention are antibodies that bind to an epitope which comprises all or a portion of an epitope recognized by the particular antibodies described herein (e.g., the same or an overlapping region or a region between or spanning the region).

Also encompassed by the present invention are antibodies that bind the same epitope and/or antibodies that compete for binding with the antibodies described herein. Antibodies that recognize the same epitope or compete for binding can be identified using routine techniques. Such techniques include, for example, an immunoassay, which shows the ability of one antibody to block the binding of another antibody to a target antigen, i.e., a competitive binding assay. Competitive binding is determined in an assay in which the immunoglobulin under test inhibits specific binding of a reference antibody to a common antigen. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual,* Cold Spring Harbor Press (1988)); solid phase direct label RIA using I-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

Other techniques include, for example, epitope mapping methods, such as, x-ray analyses of crystals of antigen: antibody complexes which provides atomic resolution of the epitope. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes.

Chimeric molecules (or fusion molecules) comprising an antigen binding domain, or equivalent, fused to another polypeptide or molecule are also encompassed by the present invention. For example, the polypeptides may be fused or conjugated to an antibody Fc region, or portion thereof (e.g., an Fc fusion protein). The antibody portion fused to a polypeptide may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603, 5,622,929, 5,359,046, 5,349,053, 5,447,851, and 5,112,946; EP 307,434; EP 367,166; PCT Publication Nos. WO 96/04388 and WO 91/06570; Ashkenazi et al., Proc. Natl. Acad. Sci. USA, 88:10535-10539 (1991); Zheng et al., J. Immunol., 154:5590-5600 (1995); and Vil et al., Proc. Natl. Acad. Sci. USA, 89:11337-11341 (1992).

As used herein, the term "immunoconjugate" refers to an antibody linked to a therapeutic moiety, such as a cytotoxin, a drug or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Antibodies use in the the present invention can be conjugated to a radioisotope, e.g., radioactive iodine, to generate cytotoxic radiopharmaceuticals for treating cancer.

Immunoconjugates can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

As used herein, the term "multivalent" refers to a recombinant molecule that incorporates more than two biologically active segments. The protein fragments forming the multivalent molecule optionally may be linked through a polypeptide linker which attaches the constituent parts and permits each to function independently.

"About" as used herein when referring to a measurable value such as an amount, a temporal duration, and the like, is meant to encompass variations of .+-.20% or .+-.10%, more preferably .+-.5%, even more preferably .+-.1%, and still more preferably .+-.0.1% from the specified value, as such variations are appropriate to perform the disclosed methods.

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by a sequence alignment program, such as BLAST, BLAST-2, ALIGN, ALIGN-2 or Megalign (DNASTAR), in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

II. PD-1 Antagonists

As used herein, the terms "Programmed Death 1," "Programmed Cell Death 1," "Protein PD-1," "PD-1," PD1," "PDCD1," "hPD-1" and "hPD-I" are used interchangeably, and include variants, isoforms, species homologs of human PD-1, and analogs having at least one common epitope with human PD-1. The complete human PD-1 sequence can be found under GenBank Accession No. U64863 (SEQ ID NO:23).

As used herein, the terms "Programmed Cell Death 1 Ligand 1", "PD-L1", " PDL1", "PDCD1L1", "PDCD1LG1", "CD274", "B7 homolog 1", "B7-H1", "B7-H", and "B7H1" are used interchangeably, and include variants, isoforms, species homologs of human PDL-1, and analogs having at least one common epitope with human PDL-1. The complete human PD-L1 amino acid sequence - isoform a precursor—can be found under GenBank Accession No. NP_054862.1 (SEQ ID NO:24). The complete human PD-L1 amino acid sequence—isoform b precursor—can be found under GenBank Accession No. NP_001254635.1 (SEQ ID NO:25).

The protein Programmed Death 1 (PD-1) is an inhibitory member of the CD28 family of receptors, that also includes CD28, CTLA-4, ICOS and BTLA. PD-1 is expressed on activated B cells, T cells, and myeloid cells (Agata et al., supra; Okazaki et al. (2002) Curr. Opin. Immunol. 14: 391779-82; Bennett et al. (2003) J Immunol 170:711-8). The initial members of the family, CD28 and ICOS, were discovered by functional effects on augmenting T cell proliferation following the addition of monoclonal antibodies (Hutloff et al. (1999) Nature 397:263-266; Hansen et al. (1980) Immunogenics 10:247-260). PD-1 was discovered through screening for differential expression in apototic cells (Ishida et al. (1992) EMBO J 11:3887-95). The other members of the family, CTLA-4 and BTLA, were discovered through screening for differential expression in cytotoxic T lymphocytes and TH1 cells, respectively. CD28, ICOS and CTLA-4 all have an unpaired cysteine residue allowing for homodimerization. In contrast, PD-1 is suggested to exist as a monomer, lacking the unpaired cysteine residue characteristic in other CD28 family members.

The PD-1 gene is a 55 kDa type I transmembrane protein that is part of the Ig gene superfamily (Agata et al. (1996) Int Immunol 8:765-72). PD-1 contains a membrane proximal immunoreceptor tyrosine inhibitory motif (ITIM) and a membrane distal tyrosine-based switch motif (ITSM) (Thomas, M. L. (1995) J Exp Med 181:1953-6; Vivier, E and Daeron, M (1997) Immunol Today 18:286-91). Although structurally similar to CTLA-4, PD-1 lacks the MYPPPY motif (SEQ ID NO: 27) that is critical for B7-1 and B7-2 binding.

Consistent with PD-1 being an inhibitory member of the CD28 family, PD-1 deficient animals develop various autoimmune phenotypes, including autoimmune cardiomyopathy and a lupus-like syndrome with arthritis and nephritis (Nishimura et al. (1999) Immunity 11:141-51; Nishimura et al. (2001) Science 291:319-22). Additionally, PD-1 has been found to play a role in autoimmune encephalomyelitis, systemic lupus erythematosus, graft-versus-host disease (GVHD), type I diabetes, and rheumatoid arthritis (Salama et al. (2003) J Exp Med 198:71-78; Prokunina and Alarcon-Riquelme (2004) Hum Mol Genet 13:R143; Nielsen et al. (2004) Lupus 13:510). In a murine B cell tumor line, the ITSM of PD-1 was shown to be essential to block BCR-mediated $Ca^{2+}$-flux and tyrosine phosphorylation of downstream effector molecules (Okazaki et al. (2001) PNAS 98:13866-71).

Two ligands for PD-1 have been identified, PD-L1 and PD-L2, that have been shown to downregulate T cell activation upon binding to PD-1 (Freeman et al. (2000) J Exp Med 192:1027-34; Latchman et al. (2001) Nat Immunol 2:261-8; Carter et al. (2002) Eur J Immunol 32:634-43). Both PD-L1 and PD-L2 are B7 homologs that bind to PD-1, but do not bind to other CD28 family members. PD-L1 is abundant in a variety of human cancers (Dong et al. (2002) Nat. Med. 8:787-9). The interaction between PD-1 and PD-L1 results in a decrease in tumor infiltrating lymphocytes, a decrease in T-cell receptor mediated proliferation, and immune evasion by the cancerous cells (Dong et al. (2003) J. Mol. Med. 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 with PD-L1, and the effect is additive when the interaction of PD-1 with PD-L2 is blocked as well (Iwai et al. (2002) Proc. Nat'l. Acad. Sci. USA 99:12293-7; Brown et al. (2003) J. Immunol. 170:1257-66).

The methods of the present invention involve the use of a PD-1 antagonist (e.g., an antibody in combination with a DR5 agonist (e.g., an antibody), for treating cancer. Accordingly, PD-1 antagonists of the invention bind to ligands of PD-1 and interfere with, reduce, or inhibit the binding of one or more ligands to the PD-1 receptor, or bind directly to the PD-1 receptor, without engaging in signal transduction through the PD-1 receptor. In one embodiment, the PD-1 antagonist binds directly to PD-1 and blocks PD-1 inhibitory signal transduction. In another embodiment the PD-1 antagonist binds to one or more ligands of PD-1 (e.g., PD-L1 and PD-L2) and reduces or inhibits the ligand(s) from triggering inhibitory signal transduction through the PD-1. In one embodiment, the PD-1 antagonist binds directly to PD-L1, inhibiting or preventing PD-L1 from binding to PD-1, thereby blocking PD-1 inhibitory signal transduction.

PD-1 antagonists used in the methods and compositions of the present invention include PD-1 binding scaffold proteins and include, but are not limited to, PD-lligands, antibodies and multivalent agents. In a particular embodiment, the antagonist is a fusion protein, such as AMP-224. In another embodiment, the antagonist is an anti-PD-1 antibody ("PD-1 antibody"). Anti-human-PD-1 antibodies (or VH and/or $V_L$ domains derived therefrom) suitable for use in the invention can be generated using methods well known in the art. Alternatively, art recognized anti-PD-1 antibodies can be used. For example, antibodies MK-3475 or CT-011 can be used. Additionally, monoclonal antibodies 5C4, 17D8, 2D3, 4H1, 4A11, 7D3, and 5F4, described in WO 2006/121168, the teachings of which are hereby incorporated by reference, can be used. Antibodies that compete with any of these art-recognized antibodies for binding to PD-1 also can be used.

An exemplary anti-PD-1 antibody is 5C4 comprising heavy and light chains having the sequences shown in SEQ ID NOs: 11 and 12, respectively, or antigen binding fragments and variants thereof. In other embodiments, the antibody comprises the heavy and light chain CDRs or variable regions of 5C4. Accordingly, in one embodiment, the antibody comprises the CDR1, CDR2, and CDR3 domains of the VH of 5C4 having the sequence set forth in SEQ ID NO: 13, and the CDR1, CDR2 and CDR3 domains of the $V_L$ of 5C4 having the sequences set forth in SEQ ID NO: 15. In another embodiment, the antibody comprises CDR1, CDR2 and CDR3 domains having the sequences set forth in SEQ ID NOs: 17, 18, and 19, respectively, and CDR1, CDR2 and CDR3 domains having the sequences set forth in SEQ ID NOs: 20, 21, and 22, respectively. In another embodiment, the antibody comprises VH and/or $V_L$ regions having the amino acid sequences set forth in SEQ ID NO: 13 and/or SEQ ID NO: 15, respectively. In another embodiment, the antibody comprises the heavy chain variable (VH) and/or light chain variable (VL) regions encoded by the nucleic acid sequences set forth in SEQ ID NO: 14 and/or SEQ ID NO: 16, respectively. In another embodiment, the antibody competes for binding with and/or binds to the same epitope on PD-1 as the above-mentioned antibodies. In another embodiment, the antibody has at least about 90% variable region amino acid sequence identity with the above-mentioned antibodies (e.g., at least about 90%, 95% or 99% variable region identity with SEQ ID NO: 13 or SEQ ID NO: 15).

In certain embodiments, the PD1 antibodies exhibit one or more desirable functional properties, such as high affinity binding to PD-1, e.g., binding to human PD-1 with a $K_D$ of $10^{-7}$M or less; lack of significant cross-reactivity to other CD28 family members, e.g., CD28, CTLA-4 and ICOS; the ability to stimulate T cell proliferation in a mixed lymphocyte reaction (MLR) assay; the ability to increase IFN-y and/or IL-2 secretion in an MLR; the ability to inhibit binding of one or more PD-1 ligands (e.g., PD-L1 and/or PD-L2) to PD-1; the ability to stimulate antigen-specific memory responses; the ability to stimulate antibody responses and/or the ability to inhibit growth of tumor cells in vivo.

In another embodiment, the PD-1 antagonist is an anti-PD-L1 antibody. Anti-human-PD-L1 antibodies (or VH and/or $V_L$ domains derived therefrom) suitable for use in the invention can be generated using methods well known in the art. Alternatively, art recognized anti-PD-L1 antibodies can be used. For example, MEDI4736 (also known as Anti-B7-H1) or MPDL3280A (also known as RG7446) can be used. Additionally, monoclonal antibodies 12A4, 3G10, 10A5, 5F8, 10H10, 1B12, 7H1, 11E6, 12B7, and 13G4 described in WO 2007/005874 and U.S. Pat. No. 7,943,743, the teachings of which are hereby incorporated by reference, can be used. Antibodies that compete with any of these art-recognized antibodies for binding to PD-L1 also can be used. An exemplary anti-PD-L1 antibody is 12A4 (WO 2007/005874 and U.S. Pat. No. 7,943,743). In one embodiment, the antibody comprises the heavy and light chain CDRs or VRs of 12A4. Accordingly, in one embodiment, the antibody comprises the CDR1, CDR2, and CDR3 domains of the VH region of 12A4 having the sequence shown in SEQ ID NO: 1 and the CDR1, CDR2 and CDR3 domains of the $V_L$ region of 12A4 having the sequence shown in SEQ ID NO: 3. In another embodiment, the antibody comprises the heavy chain CDR1, CDR2 and CDR3 domains having the sequences set forth in SEQ ID NOs: 5, 6, and 7, respectively, and the light chain CDR1, CDR2 and CDR3 domains having the sequences set forth in SEQ ID NOs: 8, 9, and 10, respectively. In another embodiment, the antibody comprises VH and/or $V_L$ regions having the amino acid sequences set forth in SEQ ID NO: 1 and/or SEQ ID NO: 3, respectively. In another embodiment, the antibody comprises the heavy chain variable (VH) and/or light chain variable (VL) regions encoded by the nucleic acid sequences set forth in SEQ ID NO: 2 and/or SEQ ID NO: 4, respectively. In another embodiment, the antibody competes for binding with, and/or binds to the same epitope on PD-L1 as, the above-mentioned antibodies. In another embodiment, the antibody has at least about 90% variable region amino acid sequence identity with the above-mentioned antibodies (e.g., at least about 90%, 95% or 99% variable region identity with SEQ ID NO: 1 or SEQ ID NO: 3).

Anti-PD-1 or anti-PD-L1 antibodies may bind to PD-1 or PD-L1, respectively, with a $K_D$ of $10^{-7}$ M, $5\times10^{-8}$ M, $10^{-8}$ M, $5\times10^{-9}$ M, $10^{-9}$ M, $5\times10^{-10}$ M, $10^{-10}$ M or less.

III. DR5 Agonists

Provided herein are methods for treating cancer comprising administering to a subject in need thereof (e.g., a subject having cancer), a therapeutically effective amount of an agent that induces apoptosis in a cancer cell and a PD-1 antagonist. Exemplary apoptosis inducing agents include DR proteins, such as DR4 and DR5.

As used herein, the terms "DR5" and "death receptor 5", also known as "tumor necrosis factor receptor superfamily member 10b", "TNFRSF10B", "CD262", "KILLER", "TRICK2", "TRICKB", "ZTNFR9", "TRAILR", "TRAILR2", "Apo-2" "TRICK2A", "TRICK2B", "TRAIL-R2", "KILLER", "KILLER/DR5", "TR6", "Tango-63", "hAPO8", and TRICK2 (see, e.g., Sheridan et al., Science, 277:818-821 (1997); Pan et al., Science, 277:815-818 (1997), WO98/51793; WO98/41629; Screaton et al., Curr. Biol., 7:693-696 (1997); Walczak et al., EMBO J., 16:5386-5387 (1997); Wu et al., Nature Genetics, 17:141-143 (1997); WO98/35986; EP870,827; WO98/46643; WO99/02653; WO99/09165; WO99/11791; US 2002/0072091; US 2002/0098550; U.S. Pat. No. 6,313,269; US 2001/0010924; US 2003/01255540; US 2002/0160446, US 2002/0048785; U.S. Pat. No. 6,342,369; U.S. Pat. No. 6,569,642, U.S. Pat. No. 6,072,047, U.S. Pat. No. 6,642,358; US 6,743,625) are used interchangeably, and include variants, isoforms, species homologs of human DR5, and analogs having at least one common epitope with DR5. The complete human DR5 sequence can be found under GenBank Accession No. AAC01565.1 (SEQ ID NO: 26).

DR5 is a member of the tumor necrosis factor (TNF) receptor superfamily. TNF ligands are known to be among the most pleiotropic cytokines, inducing a large number of cellular responses, including cytotoxicity, anti-viral activity, immunoregulatory activities, and the transcriptional regulation of several genes. Cellular responses to TNF-family ligands include not only normal physiological responses, but also diseases associated with increased apoptosis or the inhibition of apoptosis. Apoptosis (i.e., programmed cell death) is a physiological mechanism involved in the deletion of peripheral T lymphocytes of the immune system, and its dysregulation can lead to a number of different pathogenic processes. Diseases associated with increased cell survival, or the inhibition of apoptosis, include cancers, autoimmune disorders, viral infections, inflammation, graft versus host disease, acute graft rejection, and chronic graft rejection. Diseases associated with increased apoptosis include AIDS, neurodegenerative disorders, myelodysplastic syndromes, ischemic injury, toxin-induced liver disease, septic shock, cachexia and anorexia.

The death receptors are characterized by their cysteine rich domains in the extracellular region and death domains (DD) in the intracellular region. Death domain endows death receptor with function of inducing cell death by apoptosis, but sometimes it also mediates other signals. Tumor necrosis factor-related apoptosis-inducing ligand, TRAIL (Wiley S R, Schooley K, Smolak P, et al., *Immunity*, 1995, 3:673-682) in combination with its death domains triggers two cell death signaling pathways, i.e., death receptor pathway and mitochondrion pathway, to kill various tumor cells, but is nontoxic to most normal human cells.

Five TRAIL receptors, i.e., DR4 (death receptor 4 or named as TRAIL-R1), DR5, DcR1 (decoy receptor 1 or named as TRID/TRAIL-R3/LIT), DcR2 (TRAIL-R4 or named as TRUNDD), and osteoprotegerin (OPG), have been identified. Like DR4, DR5 contains three cysteine-rich domains in its extracellular portion and a single cytoplasmic death domain and be capable of signaling apoptosis upon ligand binding (or upon binding a molecule, such as an agonist (e.g., antibody), which mimics the activity of the ligand).

The term "agonist" as used with reference to DR5 refers to any molecule that partially or fully enhances, stimulates or activates one or more biological activities of DR5, in vitro, in situ, or in vivo. Examples of such biological activities binding of Apo2L/TRAIL to DR5, include apoptosis as well as those further reported in the literature. DR5 agonists may function in a direct or indirect manner. For example, the DR5 agonist may function to partially or fully enhance, stimulate or activate one or more biological activities of DR5, in vitro, in situ, or in vivo as a result of its direct binding to DR5, which causes receptor activation or signal transduction. The DR5 agonist may also function indirectly to partially or fully enhance, stimulate or activate one or more biological activities of DR5, in vitro, in situ, or in vivo as a result of, e.g., stimulating another effector molecule which then causes DR5 activation or signal transduction. It is contemplated that an agonist may act as an enhancer molecule which functions indirectly to enhance or increase DR5 activation or activity.

A DR5 agonist may be any molecule that directly or indirectly enhances the activity of DR5 and reduces tumor growth, whether on its own or in combination with another treatment, such as a PD-1 antagonist. Exemplary DR5 agonists include DR5 binding scaffolds, such as anti-DR5 antibodies ("DR5 antibodies"), e.g., chimeric, humanized or fully human antibodies, an antigen binding portion thereof, or molecules that are based on or derived from any of these. DR5 agonists may also be non-antibody proteins. DR5 agonist also include DR5 ligands, e.g., TRAIL and molecules that are derived from or based on TRAIL.

A DR5 agonist may be monovalent or multivalent. In certain embodiments, a DR5 agonist is bivalent, trivalent, tetravalent, or binds to 5, 6, 7, 8, 9, 10 or more DR5 epitopes, which may be the same or different DR5 epitopes. In certain embodiments, a DR5 agonist is a multivalent monospecific DR5 binding scaffold, e.g., a protein comprising a DR5 binding scaffold that comprises at least 2, 3, 4, 5, 6, 7, 8, 9, 10 or more regions that specifically bind to the same DR5 epitope, which binding regions may be composed of the same or a different amino acid sequence. For example, a DR5 agonist may be a DR5 binding scaffold comprising 2, 3, 4, 5, 6, 7, 8, 9, 10 or more repeats of the same DR5 binding region. Multimeric DR5 binding scaffolds are described, e.g., in WO2009/058379, WO2011/130328, WO2010/042890 and WO2011/098520.

In certain embodiments, a DR5 agonist binds specifically to DR5, but does not bind significantly or specifically to other members of the TNF receptor superfamily, such as DR4. In other embodiments, a DR5 agonist binds specifically to DR5 and DR4.

For example, in one embodiment, the DR5 agonist is a recombinant human TRAIL (TNF-related apoptosis-inducing ligand), e.g., Dulanermin (also known as AMG-951; available from Amgen/Genentech).

In another embodiment, the DR5 agonist is an antibody, e.g., an antibody that binds to human DR5 with a $K_D$ of $10^{-7}$ M, $5\times10^{-8}$ M, $10^{-8}$ M, $5\times10^{-9}$ M, $10^{-9}$ M, $5\times10^{-10}$ M, $10^{-10}$ M or less, wherein the antibody inhibits tumor growth and/or induces apoptosis of tumor cells. Numerous antibodies binding to human DR5 are known in the art and some of them have been used in clinical trials. Any of these antibodies may be used in combination with a PD-1 antagonist, provided that their combination results in inhibition of tumor growth or reduction in tumor size, e.g., in a subject having cancer. Exemplary antibodies that bind specifically to human DR5 include Conatumumab (a hTRAILR2-specific antibody also known as AMG655; available from Amgen), Drozitumab (a hTRAILR2-specific antibody also known as Apomab, DAB4, and PRO95780; available from Genentech), Lexatumumab (a hTRAILR2-specific antibody also known as HGS-ETR2; available from HGS/Kirin), Tigatuzumab (a humanized TRAILR2-specific antibody also known as CS-1008 and TRA-8; available fromDaiichi Sankyo), HGSTR2J (a hTRAILR2-specific antibody also known as KMTRS), or LBY-135 (a TRAILR2-specific Ab; available from Novartis) (see, e.g., Ashkenazi et al., Journal of Clinical Investigation 2008; 118:1979-90). In one embodiment, the DR5 agonist is a bispecific death receptor agonist antibody, see, e.g., WO2011/039126; available from Roche Glycart). In another embodiment, the DR5 agonist is an antibody conjugated to targeting peptides or a cytotoxin, Fc-human TRAIL ligand fusion (see, e.g., WO2011/039126; available from Roche Glycart). In another embodiment, the DR5 agonist is a high affinity Fc-polypeptides (see, e.g., WO2011/143614; available from Amgen).

In another embodiment, the DR5 agonist is a multivalent agent, such as TAS266 (a tetrameric nanobody agonist targeting DR5, see, e.g., WO2011/098520 and *Cancer Research* 2012;72:Supplement 1; Abstract 3852; available from Novartis and Ablynx), multimeric Tn3 protein (see, e.g., WO2009/058379, WO2011/130328, and *Cancer*

Research 2012;72:Supplement 1; Abstract 239; available from Medimmune), a multimer (e.g., a polypeptide construct with trimerizing domain and a polypeptide that binds DR5; see WO2010/042890; available from Anaphore).

Agents, which compete for binding to DR5 with any of the exemplary agents listed herein, and which inhibit tumor growth or reduces tumor size may also be used. Antibodies having VH and $V_L$ chains comprising an amino acid sequence that is at least 90%, 95%, 98% or 99% identical to those of any of the anti-DR5 antibodies listed herein may be used. In certain embodiments of the methods described herein, a DR5 agonist is replaced with a DR4 agonist. Thus, in certain embodiments, a subject having cancer is treated with a combination of a DR4 agonist and a PD-1 antagonist. Generally, any agent that induces apoptosis in tumor cells can be combined with a PD-1 antagonist for treating cancer. In certain embodiments, an apoptosis inducing agent is an agent that binds specifically to DR5 and DR4, such as TRAIL or an agent that mimics TRAIL. An exemplary DR4 agonist is Mapatumumab (HGS-ETR1), which has been used in phase 2 clinical trials.

IV. Compositions

In one aspect, the present invention provides composition comprising a PD-1 antagonist and a DR5 agonist (e.g., formulated together in a single composition or separately formulated). In one embodiment, the composition comprises a PD-1 antagonist and a DR5 agonist, wherein (a) the PD-1 antagonist is an anti-PD-1 antibody comprising the CDR1, CDR2 and CDR3 domains in a heavy chain variable region having the sequence set forth in SEQ ID NO: 13, and the CDR1, CDR2 and CDR3 domains in a light chain variable region having the sequence set forth in SEQ ID NO: 15; and (b) the DR5 agonist is an antibody. In another embodiment, the composition comprises a PD-1 antagonist and a DR5 agonist, wherein (a) the PD-1 antagonist is an anti-PD-L1 antibody comprising the CDR1, CDR2 and CDR3 domains in a heavy chain variable region having the sequence set forth in SEQ ID NO: 1, and the CDR1, CDR2 and CDR3 domains in a light chain variable region having the sequence set forth in SEQ ID NO: 3 and (b) the DR5 agonist is an antibody.

Pharmaceutical compositions suitable for administration to human patients are typically formulated for parenteral administration, e.g., in a liquid carrier, or suitable for reconstitution into liquid solution or suspension for intravenous administration.

In general, such compositions typically comprise a pharmaceutically acceptable carrier. As used herein, the term "pharmaceutically acceptable" means approved by a government regulatory agency or listed in the U.S. Pharmacopeia or another generally recognized pharmacopeia for use in animals, particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil, glycerol polyethylene glycol ricinoleate, and the like. Water or aqueous solution saline and aqueous dextrose and glycerol solutions may be employed as carriers, particularly for injectable solutions. Liquid compositions for parenteral administration can be formulated for administration by injection or continuous infusion. Routes of administration by injection or infusion include intravenous, intraperitoneal, intramuscular, intrathecal and subcutaneous.

For oral use, the pharmaceutical compositions of the present invention, may be administered, for example, in the form of tablets or capsules, powders, dispersible granules, or cachets, or as aqueous solutions or suspensions. In the case of tablets for oral use, carriers which are commonly used include lactose, corn starch, magnesium carbonate, talc, and sugar, and lubricating agents such as magnesium stearate are commonly added. For oral administration in capsule form, useful carriers include lactose, corn starch, magnesium carbonate, talc, and sugar. When aqueous suspensions are used for oral administration, emulsifying and/or suspending agents are commonly added.

In addition, sweetening and/or flavoring agents may be added to the oral compositions. For intramuscular, intraperitoneal, subcutaneous and intravenous use, sterile solutions of the active ingredient(s) are usually employed, and the pH of the solutions should be suitably adjusted and buffered. For intravenous use, the total concentration of the solute(s) should be controlled in order to render the preparation isotonic.

For preparing suppositories according to the invention, a low melting wax such as a mixture of fatty acid glycerides or cocoa butter is first melted, and the active ingredient is dispersed homogeneously in the wax, for example by stirring. The molten homogeneous mixture is then poured into conveniently sized molds and allowed to cool and thereby solidify.

Liquid preparations include solutions, suspensions and emulsions. Such preparations are exemplified by water or water/propylene glycol solutions for parenteral injection. Liquid preparations may also include solutions for intranasal administration.

Aerosol preparations suitable for inhalation may include solutions and solids in powder form, which may be in combination with a pharmaceutically acceptable carrier, such as an inert compressed gas.

Also included are solid preparations which are intended for conversion, shortly before use, to liquid preparations for either oral or parenteral administration. Such liquid forms include solutions, suspensions and emulsions.

V. Patient Populations

Provided herein are effective methods for treating cancer in a patient, e.g., using a combination of a DR5 agonist and PD-1 antagonist. In one embodiment, the patient suffers from a cancer selected from the group consisting of leukemia, lymphoma, blastoma, carcinoma and sarcoma. In another embodiment, the patient suffers from a cancer selected from the group consisting of chronic myeloid leukemia, acute lymphoblastic leukemia, Philadelphia chromosome positive acute lymphoblastic leukemia (Ph+ALL), squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, pediatric sarcoma, sinonasal natural killer, multiple myeloma, acute myelogenous leukemia (AML), and chronic lymphocytic leukemia (CML).

VI. Additional Agents/Therapies

The combinations of the present invention (e.g., PD-1 antagonist in combination with DR5 agonist) may also be used in conjunction with other well known therapies that are selected for their particular usefulness against the cancer that is being treated. Combinations of the instant invention may alternatively be used sequentially with known pharmaceutically acceptable agent(s) when inappropriate.

For example, the PD-1 antagonists and DR5 agonists described herein can further be used in combination (e.g., simultaneously or separately) with an additional treatment, such as irradiation, chemotherapy (e.g., using camptothecin (CPT-11), 5-fluorouracil (5-FU), cisplatin, doxorubicin, irinotecan, paclitaxel, gemcitabine, cisplatin, paclitaxel, doxorubicin, 5-fu, or camptothecin+apo2l/TRAIL (a 6X combo)), one or more proteasome inhibitors (e.g., bortezomib or MG132), one or more Bcl-2 inhibitors (e.g., BH3I-2' (bcl-xl inhibitor), AT-101 (R-(-)-gossypol derivative), ABT-263 (small molecule), GX-15-070 (obatoclax), or MCL-1 (myeloid leukemia cell differentiation protein-1) antagonists), iAP (inhibitor of apoptosis protein) antagonists (e.g., smac7, smac4, small molecule smac mimetic, synthetic smac peptides (see Fulda et al., *Nat Med* 2002; 8:808-15), ISIS23722 (LY2181308), or AEG-35156 (GEM-640)), HDAC (histone deacetylase) inhibitors, anti-CD20 antibodies (e.g., rituximab), angiogenesis inhibitors (e.g., bevacizumab), anti-angiogenic agents targeting VEGF and VEGFR, synthetic triterpenoids (see Hyer et al., Cancer Research 2005; 65:4799-808), c-FLIP (cellular FLICE-inhibitory protein) modulators (e.g., natural and synthetic ligands of PPARγ (peroxisome proliferator-activated receptor γ), 5809354 or 5569100), kinase inhibitors (e.g., Sorafenib), and/or genotoxic drugs.

The PD-1 antagonists and DR5 agonists described herein can further be used in combination with one or more anti-proliferative cytotoxic agents. Classes of compounds that may be used as anti-proliferative cytotoxic agents include, but are not limited to, the following:

Alkylating agents (including, without limitation, nitrogen mustards, ethylenimine derivatives, alkyl sulfonates, nitrosoureas and triazenes): Uracil mustard, Chlormethine, Cyclophosphamide (CYTOXAN™) fosfamide, Melphalan, Chlorambucil, Pipobroman, Triethylenemelamine, Triethylenethiophosphoramine, Busulfan, Carmustine, Lomustine, Streptozocin, Dacarbazine, and Temozolomide.

Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Suitable anti-proliferative agents for use in the methods of the invention, include, without limitation, taxanes, paclitaxel (paclitaxel is commercially available as TAXOL®), docetaxel, discodermolide (DDM), dictyostatin (DCT), Peloruside A, epothilones, epothilone A, epothilone B, epothilone C, epothilone D, epothilone E, epothilone F, furanoepothilone D, desoxyepothilone B1, [17]-dehydrodesoxyepothilone B, [18]dehydrodesoxyepothilones B, C12,13-cyclopropyl-epothilone A, C6-C8 bridged epothilone A, trans-9,10-dehydroepothilone D, cis-9,10-dehydroepothilone D, 16-desmethylepothilone B, epothilone B10, discoderomolide, patupilone (EPO-906), KOS-862, KOS-1584, ZK-EPO, ABJ-789, XAA296A (Discodermolide), TZT-1027 (soblidotin), ILX-651 (tasidotin hydrochloride), Halichondrin B, Eribulin mesylate (E-7389), Hemiasterlin (HTI-286), E-7974, Cyrptophycins, LY-355703, Maytansinoid immunoconjugates (DM-1), MKC-1, ABT-751, T1-38067, T-900607, SB-715992 (ispinesib), SB-743921, MK-0731, STA-5312, eleutherobin, 17beta-acetoxy-2-ethoxy-6-oxo-B-homo-estra-1,3,5(10)-trien-3-ol, cyclostreptin, isolaulimalide, laulimalide, 4-epi-7-dehydroxy-14,16-didemethyl-(+)-discodermolides, and cryptothilone 1, in addition to other microtubuline stabilizing agents known in the art.

In cases where it is desirable to render aberrantly proliferative cells quiescent in conjunction with or prior to treatment with the chemotherapeutic methods of the invention, hormones and steroids (including synthetic analogs), such as 17a-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, ZOLADEX™, can also be administered to the patient. When employing the methods or compositions of the present invention, other agents used in the modulation of tumor growth or metastasis in a clinical setting, such as antimimetics, can also be administered as desired.

Methods for the safe and effective administration of chemotherapeutic agents are known to those skilled in the art. In addition, their administration is described in the standard literature. For example, the administration of many of the chemotherapeutic agents is described in the Physicians' Desk Reference (PDR), e.g., 1996 edition (Medical Economics Company, Montvale, N.J. 07645-1742, USA); the disclosure of which is incorporated herein by reference thereto.

The chemotherapeutic agent(s) and/or radiation therapy can be administered according to therapeutic protocols well known in the art. It will be apparent to those skilled in the art that the administration of the chemotherapeutic agent(s) and/or radiation therapy can be varied depending on the disease being treated and the known effects of the chemotherapeutic agent(s) and/or radiation therapy on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

VII. Treatment Protocols

Suitable treatment protocols for treating cancer in a patient include, for example, administering to the patient an effective amount of a PD-1 antagonist (e.g., antibody) and a DR5 agonist (e.g., antibody).

As used herein, adjunctive or combined administration (co-administration) includes simultaneous administration of the antagonist and agonist in the same or different dosage form, or separate administration of the antagonist and agonist (e.g., sequential administration). Thus, the PD-1 antagonist (e.g., antibody) and DR5 agonist (e.g., antibody) can be simultaneously administered in a single formulation. Alternatively, the PD-1 antagonist and DR5 agonist can be formulated for separate administration and are administered concurrently or sequentially.

For example, the PD-1 antagonist can be administered first followed by (e.g., immediately followed by) the administration of the DR5 agonist, or vice versa. In one embodiment, the PD-1 antagonist is administered prior to administration of the DR5 agonist. In one embodiment, the DR5 agonist is administered prior to administration of the PD-1 antagonist. Such concurrent or sequential administration preferably results in both the agonist and antagonist being simultaneously present in treated patients. In another embodiment, the DR5 agonist and the PD-1 antagonist are administered simultaneously.

In an exemplary treatment, a subject is dosed with a single dose of a DR5 agonist and at least 2 doses of a PD-1 antagonist, e.g., an anti-PD-1 or anti-PD-L1 antibody. In certain embodiments, a subject receives a single dose of a DR5 agonist and at least 2, 3, 4, 5, or more doses of a PD-1 antagonist. The multiple doses of PD-1 antagonist may be provided as one dose per day, one dose every 2 days, one dose every 3 days, one dose every 4 days, one dose every 5 days or less frequently. In certain embodiments, in which a PD-1 antagonist is provided as 1 dose every 1, 2, 3, 4, 5 or more days, the single dose of DR5 agonist may be provided on a day on which the PD-1 antagonist is provided or on a day on which it is not provided. The total number of doses of PD-1 antagonist may be 2, 3, 4, 5, 6, 7, 8, 9, 10 or more.

In certain embodiments, multiple (e.g., 2, 3, 4, 5, 6, 7, 8, 9, 10 or more) doses of a DR5 agonist and multiple (e.g., 2, 3, 4, 5, 6, 7, 8, 9, 10 or more) doses of a PD-1 antagonist are administered to a subject in need of treatment. Administration of the DR5 agonist and the PD-1 antagonist may be on the same day, or alternatively, the DR5 antagonist may be administered 1 or more days before or after the PD-1 antagonist.

Administrations of a DR5 agonist and a PD-1 antagonist may also be done weekly or monthly, in which regimen, they may be administered on the same day (e.g., simultaneously), or one after the other (e.g., one or more days before or after one another)

In one embodiment, the dose of the PD-1 antagonist and/or DR5 agonist is varied over time. For example, the PD-1 antagonist and/or DR5 agonist may be initially administered at a high dose and may be lowered over time. In another embodiment, the the PD-1 antagonist and/or DR5 agonist is initially administered at a low dose and increased over time.

In another embodiment, the amount of the PD-1 antagonist and/or DR5 agonist administered is constant for each dose. In another embodiment, the amount of the PD-1 antagonist and/or DR5 agonist varies with each dose. For example, the maintenance (or follow-on) dose of the antagonist and/or agonist can be higher or the same as the loading dose which is first administered. In another embodiment, the maintenance dose of the antagonist and/or agonist can be lower or the same as the loading dose. A clinician may utilize preferred dosages as warranted by the condition of the patient being treated. The dose of may depend upon a number of factors, including stage of disease, etc. The specific dose that should be administered based upon the presence of one or more of such factors is within the skill of the artisan. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired. Intermittent therapy (e.g., one week out of three weeks or three out of four weeks) may also be used.

In one embodiment, the DR5 agonist (e.g., antibody) is administered at a dose of 0.1, 0.3, 1, 2, 3, 4, 5, 6, 7, 8, 9, or 10 mg/kg body weight. In another embodiment, the PD-1 antagonist (e.g., antibody) is administered at a dose of 0.5, 1, 2, 3, 4, 5, 6, 7, 8, 9, or 10 mg/kg body weight. Generally, 200 μg/mouse is approximately 10 mg/kg and 100 μg/mouse is approximately 5 mg/kg. Therefore, based on the experiments described herein, one or more doses of 1-20 mg/kg body weight, 1-10 mg/kg body weight, 5-20 mg/kg body weight or 5-10 mg/kg body weight of a DR5 agonist and PD-1 antagonist may be administered to a subject. In certain embodiments, a dose of 0.3 mg/kg to 10 mg/kg body weight of a DR5 agonist is used and a dose of at least 1 mg/kg, e.g., 1-100 mg/kg body weight of a PD-1 antagonist is used.

VIII. Outcomes

Patients, e.g., humans, treated according to the methods disclosed herein preferably experience improvement in at least one sign of cancer. In one embodiment, improvement is measured by a reduction in the quantity and/or size of measurable tumor lesions. In another embodiment, lesions can be measured on chest x-rays or CT or MRI films. In another embodiment, cytology or histology can be used to evaluate responsiveness to a therapy.

In one embodiment, the patient treated exhibits a reduction in size of a tumor, reduction in number of metastasic lesions over time, complete response, partial response, and stable disease. In another embodiment, the patient treated experiences tumor shrinkage and/or decrease in growth rate, i.e., suppression of tumor growth. In another embodiment, unwanted cell proliferation is reduced or inhibited. In yet another embodiment, one or more of the following can occur: the number of cancer cells can be reduced; tumor size can be reduced; cancer cell infiltration into peripheral organs can be inhibited, retarded, slowed, or stopped; tumor metastasis can be slowed or inhibited; tumor growth can be inhibited; recurrence of tumor can be prevented or delayed; one or more of the symptoms associated with cancer can be relieved to some extent.

In another embodiment, the methods of treatment produce a comparable clinical benefit rate (CBR=CR (complete response), PR (partial response) or SD (stable disease)≥6 months) better than that achieved by a PD-1 (e.g., antibody) or DR5 agonist (e.g., antibody) alone. In other embodiments, the improvement of clinical benefit rate is about 10%, 20%, 30%, 40%, 50%, 60%, 70%, 80% or more, e.g., compared to treatment with a PD-1 antagonist or DR5 agonist alone or relative to tumor growth on the first day of treatment or immediately before initiation of treatment.

In another embodiment, administration of a PD-1 antagonist and a DR5 agonist results in at least a three-fold reduction (e.g., a 3.5-fold reduction) in tumor volume, e.g., relative to treatment with the PD-1 antagonist or the DR5 agonist alone or relative to tumor growth on the first day of treatment or immediately before initiation of treatment.

In a further embodiment, administration of a PD-1 antagonist and a DR5 agonist results in tumor growth inhibition of at least 80%, e.g., relative to treatment with the PD-1 antagonist or DR5 agonist alone or relative to tumor growth on the first day of treatment or immediately before initiation of treatment.

In certain embodiments, administration of a PD-1 antagonist and a DR5 agonist reduces tumor mass by at least 10%, 20%, 30%, 40%, 50%, 60%, 70%, 80%, 90%, 95%, 99% relative to the tumor mass prior to initiation of the treatment or on the first day of treatment. In some embodiment, the tumor mass is no longer detectable following treatment as described herein. In some embodiments, a subject is in partial or full remission.

IX. Kits and Unit Dosage Forms

Also provided herein are kits which include a pharmaceutical composition containing (a) a PD-1 antagonist and (b) a DR5 agonist and a pharmaceutically-acceptable carrier, in a therapeutically effective amount adapted for use in the preceding methods. In one embodiment, the PD-1 antagonist antagonist is an antibody (e.g., 5C4 or 12A4, respectively). In another embodiment, the DR5 agonist is an antibody. The kits optionally also can include instructions, e.g., comprising administration schedules, to allow a practitioner (e.g., a physician, nurse, or patient) to administer the composition contained therein to a patient having cancer. The kit also can include a syringe.

Optionally, the kits include multiple packages of the single-dose pharmaceutical compositions each containing an effective amount of the PD-1 antagonist and the DR5 agonist for a single administration in accordance with the methods provided above. Instruments or devices necessary for administering the pharmaceutical composition(s) also may be included in the kits. For instance, a kit may provide one or more pre-filled syringes containing an amount of the PD-1 antagonist and the DR5 agonist.

In one embodiment, the present invention provides a kit for treating cancer in a patient, the kit comprising:

(a) a dose of a PD-1 antagonist;

(b) a dose of a DR5 agonist; and (c) instructions for using the PD-1 antagonist and DR5 agonist in the method of any one of claims 1-32. In another embodiment, the DR5 agonist is an antibody. In another embodiment, the PD-1 antagonist is an antibody. In particular embodiment, the PD-1 antagonist is an anti-PD-1 antibody comprising the CDR1, CDR2 and CDR3 domains in a heavy chain variable region having the sequence set forth in SEQ ID NO: 13, and the CDR1, CDR2 and CDR3 domains in a light chain variable region having the sequence set forth in SEQ ID NO: 15. In another particular embodiment, the PD-1 antagonist is an anti-PD-L1 antibody comprising antibody comprises the CDR1, CDR2 and CDR3 domains in a heavy chain variable region having the sequence set forth in SEQ ID NO: 1, and the CDR1, CDR2 and CDR3 domains in a light chain variable region having the sequence set forth in SEQ ID NO: 3.

The following examples are merely illustrative and should not be construed as limiting the scope of this disclosure in any way as many variations and equivalents will become apparent to those skilled in the art upon reading the present disclosure.

The contents of all references, Genbank entries, patents and published patent applications cited throughout this application are expressly incorporated herein by reference.

EXAMPLES

Example 1

1. Materials and Methods

Animals

Ten to eleven-week-old female C57/BL6 mice (Harlan) were used in the studies. Mice received food and water ad libitum and were maintained in a controlled environment according to Association for Assessment and Accreditation of Laboratory Animal Care (AAALAC) International regulations. All animal studies have been approved by the appropriate ethics committee and have therefore been performed in accordance with the ethical standards laid down in the 1964 Declaration of Helsinki and its later amendments.

Antibodies

Anti-mouse PD-1 mAb (anti-mPD-1 mAb) clone 4H2, mouse IgG1 isotype was produced and purified by Bristol-Myers Squibb (Biologics Discovery, CA). Agonist anti-mouse DR5 mAb, clone MD5-1, hamster IgG isotype, was purchased from BioxCell (West Lebanon, N.H.). Both antibodies were certified to have <0.5 EU/mg endotoxin levels, >95% purity and <5% high molecular weight species. Stock solutions of anti-mPD-1 mAb and anti-mDR5 antibody were kept at 4° C. prior to use. Dosing solutions of anti-mPD-1 mAb and anti-mDR5 mAb were prepared in sterile phosphate buffered saline (pH 7.0) and maintained at 4° C.

Anti-mPD-1 mAb was administered intraperitoneally at its optimal dose of 10 mg/kg; anti-DR5 mAb at 5mg/kg.

Tumor Model

The MC38 colon carcinoma tumor line used in this study was maintained in vitro. Cell suspensions were implanted in the subcutaneous space of the flank of mice of female C57/BL6 mice ($2.0 \times 10^6$ MC-38 cells in 0.2 mL Hanks Balanced Salt Solution).

Tumor size and body weights were measured twice weekly. Tumor size (measured as $mm^3$) was calculated by multiplying the tumor length by the square of the tumor width divided by 2. Treatments were initiated when subcutaneous tumors reached a median size of 200 $mm^3$ (established model). Antitumor activity, defined as percentage tumor growth inhibition, was calculated with the formula % Tumor Growth Inhibition (% TGI)=100−[(Tt/To)/(Ct/Co)]/100−(Ct/Co), where Tt=median tumor size of treated group at the end of treatment, To =median tumor size of treated group at treatment initiation, Ct=median tumor size of control group at the end of treatment, and Co=median tumor size at treatment initiation (see Table 3). Complete regressions were defined as absence of measurable tumor mass for at least 2 tumor volume doubling times.

The tumor response endpoint was expressed as tumor growth delay (T–C value), calculated as the difference in time (days) between the treated (T) and control (C) groups for the tumor to reach a predetermined target size. A delay in reaching target size by the treated groups of >1 times tumor volume doubling time was considered an active result. Therapeutic synergy was defined as an antitumor effect in which the combination of agents demonstrated significant superiority (p<0.05) relative to the activity shown by each agent alone.

The antitumor effect of single dose anti-mouse DR5 mAb in combination an anti-PD-1 mAb given at various dose schedules was evaluated in MC-38 (murine colon) tumor bearing mice. Six days post tumor implant, mice were sorted into eight groups of 7 mice with a mean tumor volume of ~200 $mm^3$. Antibodies were administered according to the dosing schedules descried in Table 1.

TABLE 1

| Dosing Schedule | |
|---|---|
| Treatment Group | # mice |
| 1: Control | 7 |
| 2: Control + anti-PD-1 mAb; 200 ug/mouse; Q4D × 3 dosing initiated day 6 | 7 |
| 3: Control + anti-PD-1 mAb; 200 ug/mouse; Q4D × 3 dosing initiated day 8 | 7 |
| 4: Control + anti-PD-1 mAb; 200 ug/mouse; Q4D × 3 dosing initiated day 9 | 7 |
| 5: Anti-DR5 mAb; 100 ug/mouse; QD + Control dosing initiated day 8 | 7 |
| 6: Anti-DR5 mAb; 100 ug/mouse dosed day 8; QD + anti-PD-1 mAb; 200 ug/mouse; Q4D × 3 dosed day 6 | 7 |
| 7: Anti-DR5 mAb; 100 ug/mouse dosed day 8; QD + anti-PD-1 mAb; 200 ug/mouse; Q4D × 3 dosed day 8 | 7 |
| 8: Anti-DR5 mAb; 100 ug/mouse dosed day 8; QD + anti-PD-1 mAb; 200 ug/mouse; Q4D × 3 dosed day 9 | 7 |

QD: One dose administered on only one day.
Q4D × 3: One dose administered every four days for a total of 3 doses.

The combination of DR5 mAb and PD-1 mAb were tested according to the three schedules set forth in Table 2.

TABLE 2

Administration Schedules

| Group No.: | Administration Schedule |
|---|---|
| Group 6 | DR5 mAb was administered 2 days after PD-1 mAb therapy. |
| Group 7 | DR5 mAb and PD-1 mAb were administered on the same day. |
| Group 8 | DR5 mAb was administered 1 day before PD-1 mAb therapy. |

It was hypothesized that since PD-1 mab induces IFN-gamma, which in tumors upregulates DR5 expression on tumor cells, it might be advantageous to administer the DR5 mAb after administration of PD-1 mAb therapy (Group 6). Alternatively, it was hypothesized that DR5 mAb induces tumor cell death, which in turn will prime antitumor immune responses, and PD-1 mAb will subsequently expand the induced antitumor immunity. To test this hypothesis, DR5 mAb was administered before PD-1 mAb therapy (Group 8).

2. Results

As shown in Table 3, at least 80% tumor growth inhibition was achieved in mice treated with a combination of both the DR5 mAb and PD1 mAb.

TABLE 3

Tumor Responses

| Treatment | Dose (mg/kg) | Schedule (days post implant) | % TGI | % Complete Regressions (#/total mice) |
|---|---|---|---|---|
| Anti-PD-1 mAb | 10 | Day 6, 10, 14 | 31 | 0 (0/7) |
| Anti-PD-1 mAb | 10 | Day 8, 12, 16 | 14 | 0 (0/7) |
| Anti-PD-1 mAb | 10 | Day 9, 13, 17 | −8 | 0 (0/7) |
| Anti-DR5 mAb | 5 | Day 8 | −4 | 0 (0/7) |
| Anti-PD-1 mAb + Anti-DR5 mAb | 10 5 | Day 6, 10, 14 Day 8 | 96 | 43 (3/7) |
| Anti-PD-1 mAb + Anti-DR5 mAb | 10 5 | Day 8, 12, 16 Day 8 | 82 | 14 (1/7) |
| Anti-PD-1 mAb + Anti-DR5 mAb | 10 5 | Day 9, 13, 17 Day 8 | 87 | 43 (3/7) |

Moreover, as shown in FIG. 1, the medium tumor volume (measured in $mm^3$) in mice treated with a combination of the DR5 mAb and the PD-1 mAb was significantly reduced, compared to mice treated with a control or either agent alone. Specifically, there was about a 3.5 fold reduction (e.g., at least a 3 fold reduction) in tumor volume in mice treated with both the DR5 mAb and the PD-1 mAb, compared to mice treated with a control or either agent alone. The tumor volume in individual mice is shown in FIGS. 2A-2H.

Figure 3:
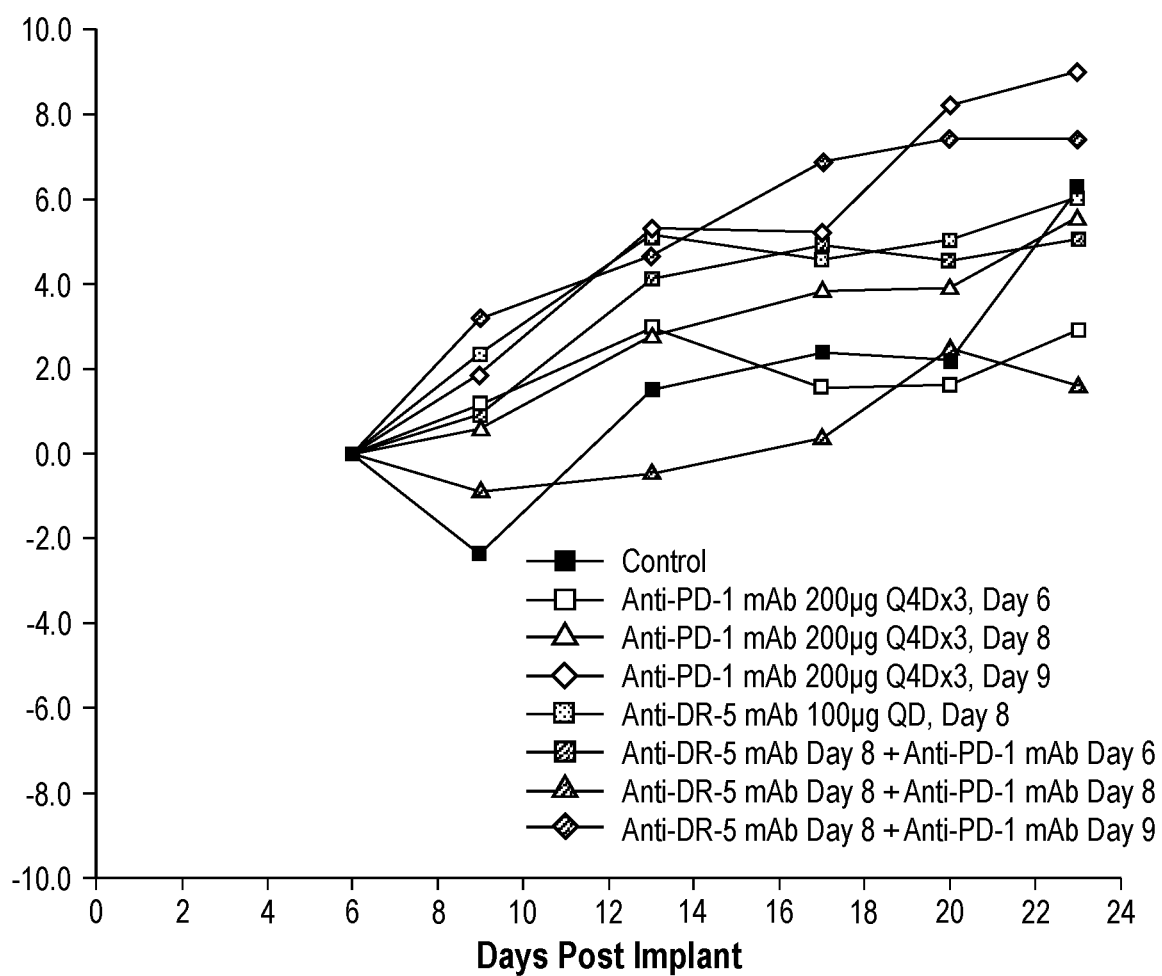
FIG. 3 is a graph depicting the percent body weight change following administration of a control, an anti-DR5 monoclonal antibody, an anti-PD-1 antibody, or combination of both an anti-DR5 monoclonal antibody and anti-PD-1 antibody, up to 24 days post implant.

In sum, the combination of the DR5 mAb and the PD-1 mAb resulted in enhanced activity compared to the activity elicited by single agents alone, independent of the schedule utilized. This synergy was statistically significant ($p<0.05$, Wilcoxon). Out of the 3 administration schedules tested, a trend for better activity was observed in the groups which were treated with anti-mDR5 first or with anti-mPD-1 first. As shown in FIG. 3, the combination therapy was well-tolerated (no significant body weight loss). In previous studies, significant body weight loss (>20%) was observed with multiple doses of the DR5 mAb alone or in combination.

Therefore, results from this study demonstrate that a combination regimen that includes a single dose of anti-mDR5 mAb and multiple doses of PD-1 mAb is well-tolerated and result in marked antitumor activity.

What is claimed is:

1. A method of treating cancer in a subject in need of treatment, wherein the cancer is a cancer selected from the group consisting of leukemia, lymphoma, blastoma, carcinoma and sarcoma, the method comprising administering to the subject (a) at least two doses of 1-100 mg/kg body weight of an antagonist antibody that binds human programmed cell death 1 (PD-1) and (b) at least one dose of 0.1-10 mg/kg body weight of an agonist antibody that binds human tumor necrosis factor (TNF)-related apoptosis-inducing ligand receptor 2 (TRAIL-R2 or DR5), wherein the cancer is treated by the administration of the antibodies; and wherein the PD-1 antibody comprises the CDR1, CDR2 and CDR3 domains in a heavy chain variable region having the sequence set forth in SEQ ID NO: 13, and the CDR1, CDR2 and CDR3 domains in a light chain variable region having the sequence set forth in SEQ ID NO: 15.

2. The method of claim 1, wherein the DR5 antibody is selected from the group consisting of Lexatumumab, Tigatuzumab, Conatumumab, Drozitumab, HGSTR2J/KMTRS, and LBY-135.

3. The method of claim 1, wherein the PD-1 antibody comprises:
   (a) a heavy chain variable region CDR1 having the sequence set forth in SEQ ID NO: 17;
   (b) a heavy chain variable region CDR2 having the sequence set forth in SEQ ID NO: 18;
   (c) a heavy chain variable region CDR3 having the sequence set forth in SEQ ID NO: 19;
   (d) a light chain variable region CDR1 having the sequence set forth in SEQ ID NO: 20;
   (e) a light chain variable region CDR2 having the sequence set forth in SEQ ID NO: 21; and
   (f) a light chain variable region CDR3 having the sequence set forth in SEQ ID NO: 22.

4. The method of claim 1, wherein the PD-1 antibody comprises heavy and light chain variable regions having the sequences set forth in SEQ ID NOs: 13 and 15, respectively.

5. The method of claim 1, wherein the PD-1 antibody comprises heavy and light chains having the sequences as set forth in SEQ ID NOs: 11 and 12, respectively.

6. The method of claim 1, wherein administration of the PD-1 antibody and DR5 antibody reduces tumor size by at least 50%, compared to the tumor size prior to administration.

7. The method of claim 1, wherein the PD-1 antibody is administered before the DR5 antibody.

8. The method of claim 1, wherein the DR5 antibody is administered before the PD-1 antibody.

9. The method of claim 1, which comprises administration of an additional therapeutic agent.

10. The method of claim 1, wherein the cancer is carcinoma.

11. The method of claim 1, wherein the cancer is colon carcinoma.

12. A method of treating cancer in a subject in need of treatment, wherein the cancer is a cancer selected from the group consisting of leukemia, lymphoma, blastoma, carcinoma and sarcoma, the method comprising administering to the subject (a) at least two doses of an effective amount of a PD-1 antibody comprising the CDR1, CDR2 and CDR3 domains in a heavy chain variable region having the sequence set forth in SEQ ID NO: 13, and the CDR1, CDR2 and CDR3 domains in a light chain variable region having the sequence set forth in SEQ ID NO: 15 and (b) at least one dose of an effective amount of a DR5 antibody selected from the group consisting of Lexatumumab, Tigatuzumab, Conatumumab, Drozitumab, HGSTR2J/KMTRS, and LBY-135, wherein the cancer is treated by the administration of the antibodies.

13. The method of claim 12, wherein the cancer is carcinoma.

14. The method of claim 13, wherein the cancer is colon carcinoma.

* * * * *

UNITED STATES PATENT AND TRADEMARK OFFICE
CERTIFICATE OF CORRECTION

PATENT NO. : 11,103,579 B2
APPLICATION NO. : 15/993687
DATED : August 31, 2021
INVENTOR(S) : Bryan Barnhart et al.

It is certified that error appears in the above-identified patent and that said Letters Patent is hereby corrected as shown below:

On the Title Page

At Column 1, in item (56), Line 4 of the "U.S. Patent Documents" section, delete "1,763,223" and insert --5,763,223--.

Signed and Sealed this
Twelfth Day of December, 2023

Katherine Kelly Vidal
*Director of the United States Patent and Trademark Office*